(12) United States Patent
Sano et al.

(10) Patent No.: US 10,137,014 B2
(45) Date of Patent: Nov. 27, 2018

(54) STENT

(71) Applicant: NIPRO CORPORATION, Osaka (JP)

(72) Inventors: Yoshihiko Sano, Osaka (JP); Yasushi Ooyama, Osaka (JP); Katsuhiro Hiejima, Osaka (JP); Kouji Akimoto, Osaka (JP)

(73) Assignee: NIPRO Corporation, Osaka (JP)

( * ) Notice: Subject to any disclaimer, the term of this patent is extended or adjusted under 35 U.S.C. 154(b) by 0 days.

(21) Appl. No.: 15/103,645

(22) PCT Filed: Dec. 16, 2014

(86) PCT No.: PCT/JP2014/083308
§ 371 (c)(1),
(2) Date: Jun. 10, 2016

(87) PCT Pub. No.: WO2015/098629
PCT Pub. Date: Jul. 2, 2015

(65) Prior Publication Data
US 2016/0317331 A1    Nov. 3, 2016

(30) Foreign Application Priority Data

Dec. 24, 2013 (JP) ................................ 2013-264823
Feb. 25, 2014 (JP) ................................ 2014-034486
(Continued)

(51) Int. Cl.
*A61F 2/82* (2013.01)
*A61F 2/89* (2013.01)
(Continued)

(52) U.S. Cl.
CPC ................ *A61F 2/89* (2013.01); *A61F 2/915* (2013.01); *A61F 2/856* (2013.01);
(Continued)

(58) Field of Classification Search
CPC .... A61F 2/82; A61F 2/89; A61F 2/915; A61F 2250/0014; A61F 2250/0026;
(Continued)

(56) References Cited

U.S. PATENT DOCUMENTS

| 5,718,713 A | 2/1998 | Frantzen |
| 2002/0038767 A1 | 4/2002 | Trozera |

(Continued)

FOREIGN PATENT DOCUMENTS

| CN | 1306407 A | 8/2001 |
| CN | 101952341 A | 1/2011 |

(Continued)

OTHER PUBLICATIONS

International Search Report in corresponding International Patent Application No. PCT/JP2014/083308, dated Mar. 23, 2015, with English Translation.

(Continued)

*Primary Examiner* — Howie Matthews
(74) *Attorney, Agent, or Firm* — Edell, Shapiro & Finnan, LLC

(57) ABSTRACT

A stent (32) configured to be placed in a body lumen and having a tubular shape formed by a structure that is expandable and contractible skeleton (18, 19) in a radial direction, the skeleton (18, 19) having a heteromorphic structure due to changes of a cross section shape thereof in a thickness direction. A stent (10) that is expandable and contractible in the radial direction while being configured to be placed in a body lumen, the stent (10) having a heteromorphic tubular shape, a cross section shape of which changes in a lengthwise direction, and having a metal skeleton (18, 19) formed by at least one of electroforming and etching.

21 Claims, 15 Drawing Sheets
(3 of 15 Drawing Sheet(s) Filed in Color)

(30) Foreign Application Priority Data

Aug. 25, 2014 (JP) ................................ 2014-170640
Aug. 25, 2014 (JP) ................................ 2014-170644

(51) Int. Cl.
- *A61F 2/915* (2013.01)
- *A61F 2/856* (2013.01)

(52) U.S. Cl.
CPC .................. A61F 2002/9155 (2013.01); A61F 2002/91525 (2013.01); A61F 2002/91541 (2013.01); A61F 2002/91575 (2013.01); A61F 2210/0076 (2013.01); A61F 2230/006 (2013.01); A61F 2230/0023 (2013.01); A61F 2230/0067 (2013.01); A61F 2230/0078 (2013.01); A61F 2250/0018 (2013.01); A61F 2250/0036 (2013.01); A61F 2250/0039 (2013.01); A61F 2250/0068 (2013.01)

(58) Field of Classification Search
CPC .............. A61F 2250/0036–2250/00395; A61F 2002/91525; A61F 2230/0023; A61F 2250/0018; A61F 2250/0029
See application file for complete search history.

(56) References Cited

U.S. PATENT DOCUMENTS

| | | | |
|---|---|---|---|
| 2003/0144725 | A1 | 7/2003 | Lombardi |
| 2007/0100431 | A1 | 5/2007 | Bonsignore et al. |
| 2010/0076556 | A1* | 3/2010 | Tomantschger ........ A61L 17/10 623/11.11 |
| 2012/0071962 | A1 | 3/2012 | Huang et al. |
| 2013/0138204 | A1 | 5/2013 | Kinuta et al. |

FOREIGN PATENT DOCUMENTS

| | | | |
|---|---|---|---|
| CN | 102605390 A | 7/2012 | |
| CN | 103079605 A | 5/2013 | |
| JP | 2003-520055 A | 7/2003 | |
| JP | 2003-521995 A | 7/2003 | |
| JP | 2005-021504 A | 1/2005 | |
| JP | 2007-125394 A | 5/2007 | |
| JP | 2007-267844 A | 10/2007 | |
| JP | 2008-518681 A | 6/2008 | |
| WO | 2004037126 A2 | 5/2004 | |
| WO | 2006011523 A1 | 2/2006 | |
| WO | 2008073496 A2 | 6/2008 | |
| WO | 2009070624 A1 | 6/2009 | |
| WO | 2009099559 A2 | 8/2009 | |
| WO | 2009152376 A1 | 12/2009 | |
| WO | 2011021566 A1 | 2/2011 | |
| WO | 2012071075 A1 | 5/2012 | |
| WO | 2013040373 A1 | 3/2013 | |
| WO | 2014013444 A2 | 1/2014 | |

OTHER PUBLICATIONS

Office Action issued in Chinese Application No. 201480070564.0 dated Feb. 28, 2017 with English language translation.
English Translation of the International Preliminary Report on Patentability issued in corresponding International Patent Application No. PCT/JP2014/083308, dated Jul. 7, 2016.
Office Action for corresponding Chinese Patent Application 201480070564.0 dated Oct. 23, 2017 with translation.
European Search Report issued in European Patent Application No. 14874864.3 dated Jul. 18, 2017.
Office Action issued in Japanese Application No. 2014-170644 along with an English language translation, dated Jan. 31, 2018.
Office Action issued in Japanese Application No. 2014-170640 along with an English language translation, dated Feb. 1, 2018.
European Office Action from corresponding European Patent Application No. 14874864.3 dated May 2, 2018, 6 pages.
Chinese Office Action with English translation from corresponding Chinese Patent Application No. 201480070564.0 dated Apr. 20, 2018, 20 pages.
Japanese Office Action including English-language translation on the corresponding Japanese Patent Application No. 2014-170644, dated Jul. 5, 2018, 7 pages.

* cited by examiner

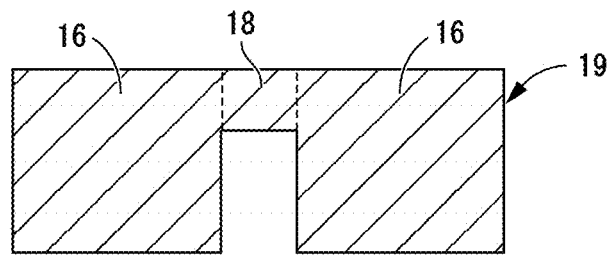
FIG.5A
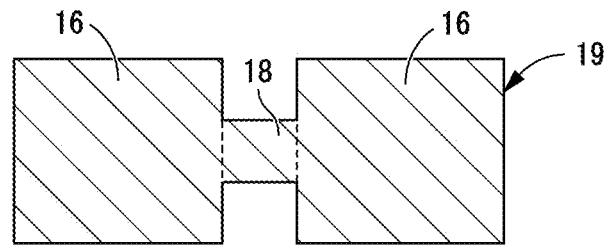
FIG.5B
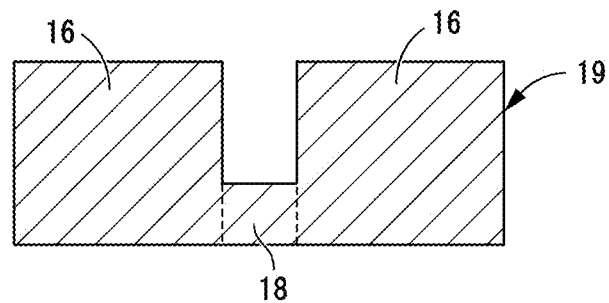
FIG.5C
FIG.6
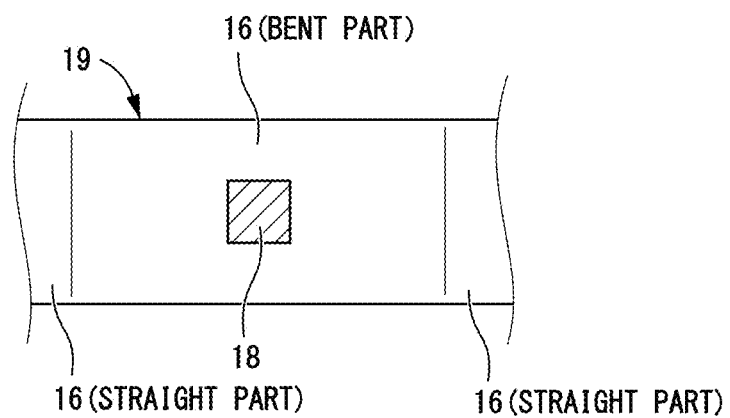

FIG. 7
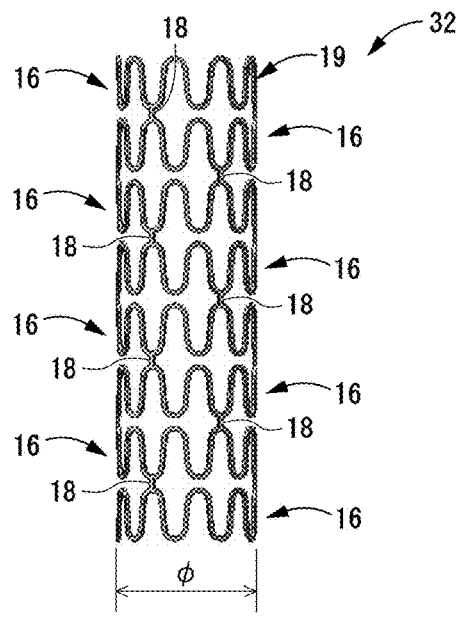
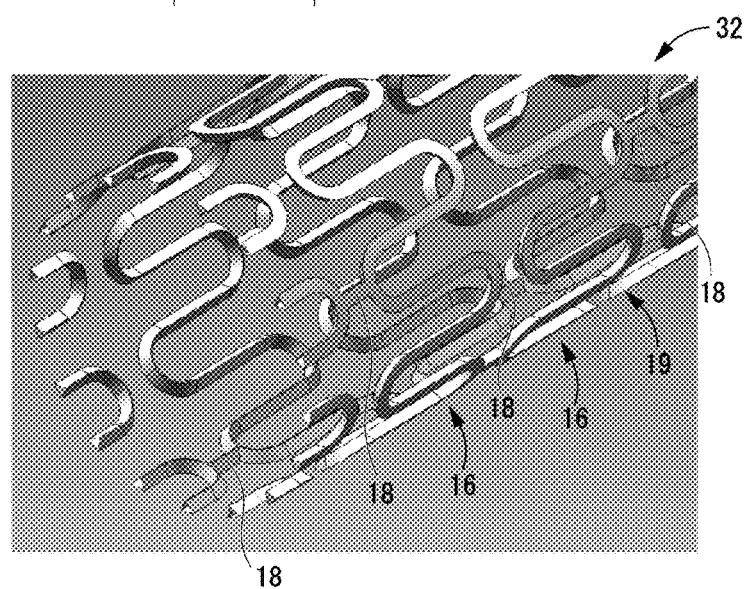
FIG. 8A
FIG. 8B
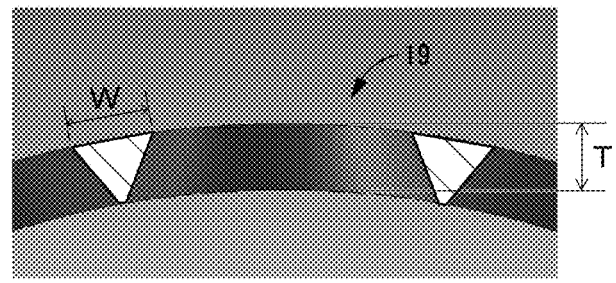

PRIOR ART

FIG.16
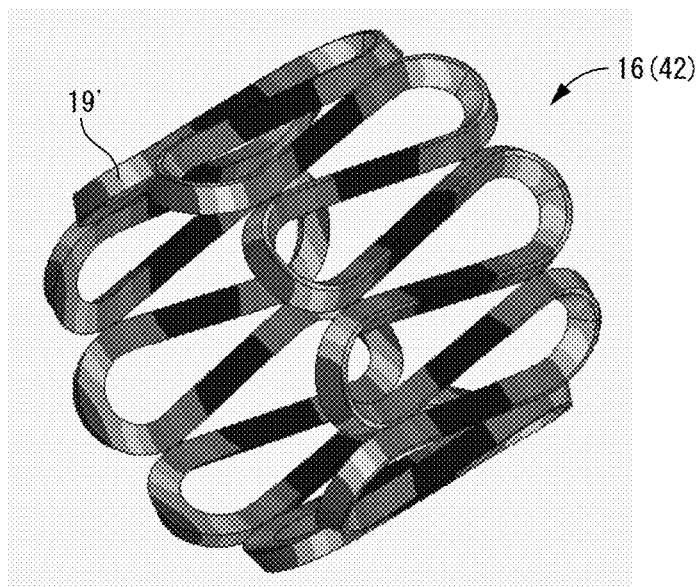
FIG.17A  FIG.17B
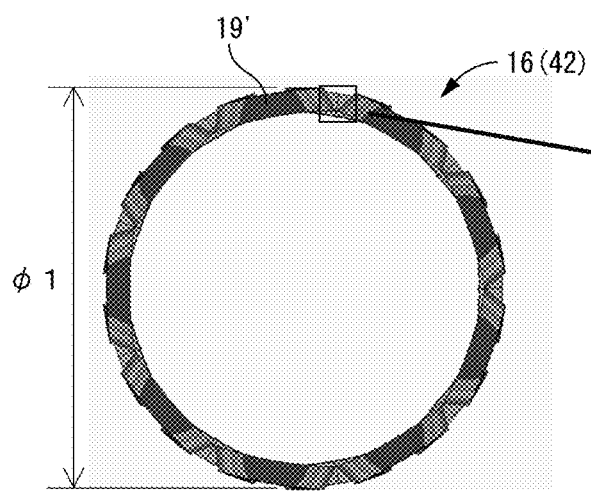 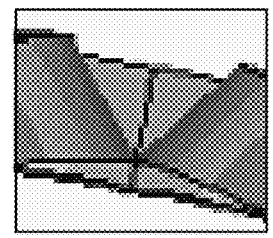

PRIOR ART

PRIOR ART

STENT

CROSS REFERENCE TO RELATED APPLICATIONS

This application is 371 National Stage of International Application No. PCT/JP2014/083308, filed on Dec. 16, 2014, and claims priority under 35 U.S.C. § 119 to Application No. JP 2014-170644 filed on Aug. 25, 2014, Application No. JP 2014-170640 filed on Aug. 25, 2014, Application No. JP 2014-034486 filed on Feb. 25, 2014, Application No. JP 2013-264823 filed on Dec. 24, 2013, the entire contents of which are hereby incorporated by reference.

TECHNICAL FIELD

The present invention relates to a stent inserted and placed in a body lumen such as a blood vessel or the like.

BACKGROUND ART

Conventionally, when an abnormality such as stenosis, occlusion or the like occurs in a lumen such as a blood vessel or the like, stent treatment has been performed by inserting the stent within the lumen and holding the lumen in an expanded state, for example. The stent overall has a tubular shape, and has a small diameter when inserted in the lumen, but is placed with the diameter enlarged within the lumen. As a method for expanding the stent within the lumen, in addition to expansion using a balloon, there is also self expansion using shape memory materials or the like, mechanical expansion, and the like.

Also, in addition to making it possible for the stent to be deformed by expansion or contraction as described above, in consideration of reducing the burden on the living body, improving biocompatibility and the like, a porous structure with many through holes provided in the peripheral wall part or a strut structure connected linearly is used. In specific terms, for example as noted in Japanese Unexamined Patent Publication No. JP-A-2007-267844 (Patent Document 1) or the like, in addition to cutting a metal tube of stainless steel, platinum or the like to a suitable length, by forming through holes or a strut using laser processing on the peripheral wall, the stent is constituted for which the strut cross section shape is a simple rectangular shape.

However, with a stent of the conventional structure for which the strut has a simple rectangular cross section shape, it was still difficult to obtain sufficient freedom of design to realize compatibility considering suitability for each patient and the like, and it was hard to say that the required characteristics at medical sites could be sufficiently handled.

In specific terms, when stent treatment is performed with a stent of the conventional structure placed at the stenosis portion of a patient with arteriosclerosis, for example, though the expanded state of the blood vessel is maintained immediately after the stent is placed, at several weeks to several months after the surgery, by a clot adhering to the stent, there were cases of restenosis occurring at the blood vessel in the position at which the stent was placed. The existence and degree of restenosis depends on things like the portion at which the stenosis occurred, the status at that stenosis portion, the patient, and the like, thus improvement and handling thereof was difficult with stents of the conventional structure.

In addition, when expanding the stent with a balloon or the like to place it within a blood vessel, there were cases when the stent had its position displaced within the blood vessel in the lengthwise direction. The existence and degree of positional displacement of the stent within the blood vessel also differs according to the site and status of the portion at which the stent was placed, the patient, and the like, so that improvement and handling thereof was also difficult with stents of the conventional structure.

Furthermore, with this kind of stent of the conventional structure, a metal tube which is an element tube has a simple, straight, round tubular shape. Thus, it was difficult to make a shape to correspond to the placement portion in a lumen such as a blood vessel or the like. Therefore, with the lumen, for example, in a portion for which the inner diameter dimension changes with a tapered shape, or a bifurcated portion such as a bifurcation or the like, there was the problem that it was difficult to prepare a stent that precisely matched the shape of the lumen.

In fact, when doing laser processing on the element tube to form through holes or a strut, when there is a large area to be cut, there is the problem that the yield becomes poor. To increase the yield, there was also the idea of taking a stent obtained by implementing laser processing on a small diameter, round tubular element tube, reducing the diameter and inserting it in the lumen, and then enlarging the diameter to be larger than the initial element tube diameter for placement. However, there was the risk that distortion and residual stress in the enlarged diameter state would become great, and it would not be possible to obtain a stable shape and durability.

Also, it is likely for roughness such as burrs to occur at the portion at which laser processing was done, meaning that post-processing either chemically or mechanically is required. This poses the problem that manufacturing becomes complex, and precise management of post-processing and the like would be difficult.

BACKGROUND ART DOCUMENT

Patent Document

Patent Document 1: JP-A-2007-267844

SUMMARY OF THE INVENTION

Problem the Invention Attempts to Solve

The present invention has been developed in view of the above-described matters as the background, and it is an object of the present invention noted in claim 1 to provide a stent with a novel structure which is able to adjust with an even greater degree of freedom of design the stent performance and the like according to the portion at which stenosis occurs within the lumen in which the stent is placed, the status of that stenosis portion, and the like.

Also, it is an object of the present invention noted in claim 5 to provide a stent of a novel structure which is able to realize with good yield a shape corresponding to the lumen such as a blood vessel or the like.

Means for Solving the Problem

A first mode of the present invention provides a stent having a tubular shape through a structure of a skeleton that is expandable and contractible in a radial direction while being configured to be placed in a body lumen, characterized in that the skeleton has a heteromorphic structure due to changes of a cross section shape thereof in a thickness direction.

With the stent constituted according to this mode, by making the cross section shape of the skeleton different from the conventional simple rectangular cross section shape, it is possible to perform, with a great deal of freedom of design as well as efficiently, adjustment of the performance of the stent and the like according to the portion at which the stenosis occurs within the lumen in which the stent is placed as well as to the status of that stenosis portion and the like.

A second mode of the present invention provides the stent according to the first mode, wherein with the cross section shape of the skeleton, a width dimension becomes larger from an inner circumference surface thereof toward an outer circumference surface thereof.

With the stent constituted according to this mode, compared to the stent of the conventional structure which has the skeleton with the simple rectangular cross section, it is possible to make the width dimension of the cross section of the part exposed to the fluid in the lumen such as blood or the like smaller. By so doing, at the position at which the stent is placed within the lumen such as a blood vessel or the like, compared to a stent of the conventional structure, blood or the like flows more easily, and stagnation or turbulence of blood or the like can be inhibited. As a result, it is possible to effectively avoid problems such as the formation of clots, the adherence of the clot to the stent, and restenosis occurring with the blood vessel at the position at which the stent is placed or the like.

Also, at the outer circumference surface of the stent, the width dimension of the cross section of the skeleton is ensured to be relatively large in the circumference direction. Thus, it is possible to have the pressing force on the lumen inner surface of the blood vessel or the like be dispersed, thereby inhibiting the occurrence of cracks of the lumen wall due to local force concentration, while shortening the healing period for cracks that occur in the lumen wall. By so doing, it is possible to effectively inhibit restenosis due to hypertrophy of vascular endothelial cells at blood vessel crack portions, for example. Even if there is hypertrophy of the vascular endothelial cells, at the stent inner circumference surface side, by providing a relatively large gap between skeletons for which the width dimension of the cross section has been made smaller, hypertrophy of the vascular endothelial cells further toward the inside from the stent inner circumference surface is inhibited, and a further inhibitory effect on blood vessel restenosis is exhibited.

Furthermore, with the stent constituted according to this mode, since the circumferential width dimension of the skeleton cross section becomes smaller toward the inner circumference side, when a delivery catheter is mounted and the diameter is reduced, the problem of adjacent skeletons in the circumference direction mutually abutting at the inner circumference side with the small circumferential length and the diameter reduction volume thereof being limited is eliminated. Therefore, while ensuring the cross section area of the skeleton and realizing the required strength and the like, it is possible to set the dimension to which the diameter can be reduced to be sufficiently small to improve delivery performance.

With the stent of this mode, with the cross section shape of the skeleton, there are no limitations as long as the width dimension becomes larger toward the outer circumference surface from the inner circumference surface. However, it is particularly preferable for the cross section shape to have roughly a reverse triangle shape, and more preferable to have roughly a reverse isosceles triangle shape.

A third mode of the present invention provides the stent according to the first or second mode, wherein with the cross section shape of the skeleton, an included angle of both side surfaces in a circumference direction is greater than a central angle of an arc of an outer circumference surface thereof.

With the stent constituted according to this mode, in the state before diameter reduction, both side surfaces in the circumference direction of the skeleton cross section enter in the direction of mutually approaching further to the inner circumference side than the radial direction line. Therefore, even when the diameter is reduced, it is possible to avoid having the adjacent skeletons in the circumference direction abut each other early at the inner circumference side, thus having the diameter reduction volume limited. As a result, the circumference direction length of the skeleton at the stent outer circumference surface is ensured, and while avoiding local pressing force acting on the blood vessel or the like, it is possible to realize a stent for which it is possible to have diameter reduction deformation to an even smaller diameter dimension.

A fourth mode of the present invention provides the stent according to any of the first to third modes, wherein the skeleton is a metal skeleton formed by at least one of electroforming and etching.

With the stent constituted according to this mode, by the skeleton being formed using electroforming or etching, the shape corresponds to the lumen shape from the start. Therefore, compared to a stent manufactured by laser processing, it is possible to have less cutting part, and to manufacture the stent with good yield.

Also, by combining this with the eighth mode described later, adjustment of the end part rigidity can be realized by making the thickness dimension larger, by using different material properties, or the like. Furthermore, by combining this with the eleventh mode described later, using electroforming or etching, it is possible to form weak parts simultaneously with other parts of the skeleton, so post-processing of weak parts is not necessary, and provision with a high level of dimensional precision is possible.

A fifth mode of the present invention provides a stent that is expandable and contractible in a radial direction while being configured to be placed in a body lumen, characterized in that the stent has a heteromorphic tubular shape whose cross section shape changes in a lengthwise direction, and includes a metal skeleton formed by at least one of electroforming and etching.

With the stent constituted according to this mode, in contrast to the item obtained by laser processing the element tube of the conventional structure, by using the skeleton formed by electroforming or etching, the shape corresponding to the lumen shape is given from the start. Therefore, compared to the stent made by laser processing of the conventional structure, it is possible to have less cutting part, and to manufacture a stent with good yield.

Therefore, even in a case when it is placed in a heteromorphic lumen such as a blood vessel or the like, a shape that precisely corresponds to the lumen is realized, so that the labor burden of the procedure on the practitioner is reduced, and for the patient, the burden on the living body and the like is reduced. Also, with the stent itself placed in the shape corresponding to the lumen, distortion and residual stress are reduced, and it is possible to realize good shape stability and durability.

A sixth mode of the present invention provides the stent according to the fifth mode, wherein a bifurcation is provided so that the stent has the heteromorphic tubular shape for which a number of tube parts changes in the lengthwise direction.

With the stent constituted according to this mode, a stent is realized that can easily be used for a bifurcated part such as a bifurcation for a lumen such as a blood vessel or the like.

A seventh mode of the present invention provides the stent according to the fifth or sixth mode, wherein the stent has the heteromorphic tubular shape for which a diameter dimension changes in the lengthwise direction.

With the stent constituted according to this mode, it is possible to realize a stent that can be applied suitably to a portion such as for which the inner diameter of the lumen such as a blood vessel or the like changes in the lengthwise direction. By the stent of this mode being combined with the sixth mode, the stent with a bifurcation can have at least one tube part be a tapered tube shape or the like.

An eighth mode of the present invention provides the stent according to any of the first to seventh modes, wherein at least one end part thereof in an axial direction has a greater rigidity than that of a center part thereof.

With the stent constituted according to this mode, for example when formed by electroforming, by making the thickness dimension of specific parts in the lengthwise direction larger, or by using different material properties or the like, the rigidity can be adjusted. In particular with the stent of this mode, by making the rigidity greater for the axial end parts for which deformation occurs easily due to structural reasons, it is possible to effectively prevent the axial end parts from separating from the lumen in a state placed in the lumen to become a cause of restenosis, for example.

Specifically, for example, by having the axial end parts in a state placed in the blood vessel separated from that blood vessel, there is an increase in the risk of a clot forming due to turbulence of the blood flow being caused. Therefore, by increasing the rigidity of the axial end parts of the stent and stabilizing for placement in the blood vessel, it is possible to effectively prevent restenosis at the position at which the stent is placed.

A ninth mode of the present invention provides the stent according to the eighth mode, wherein the end part for which the rigidity is greater than that of the center part has a smaller rigidity at a terminal part thereof at an axial outside.

With the stent constituted according to this mode, the rigidity of the terminal part at the end part of the stent is made smaller, so that it is possible to suppress the load placed on the lumen by the terminal part of the stent. When the skeleton is formed using metal, adjustment of the rigidity at the terminal part can be realized by forming only the terminal part of the stent using a soft metal, or by making the wall thickness dimension or the width dimension smaller. Also, preferably, the rigidity of the terminal part is set to be roughly the same or smaller than that of the center part.

A tenth mode of the present invention provides the stent according to any of the first to ninth modes, wherein the skeleton has a laminated structure of a plurality of types of metals.

With the stent constituted according to this mode, it is possible to form the laminated structure of a plurality of types of metal by electroforming, for example. For example, by using a metal material with greater ductility at the surface layer than at the core layer, while ensuring stent strength with the core layer, it is possible to ease surface stress when doing expansion/contraction or deformation of the stent, making it possible to prevent the occurrence of cracks or the like. Also, by using a metal material with smaller ionization tendency at the surface layer than at the core layer, while ensuring the required strength characteristics at the core layer, it is possible to realize biocompatibility, radiopaqueness and the like at the surface. With this mode, it is sufficient if at least one part of the skeleton uses a laminated structure, and it is not necessary that the entire skeleton uses a laminated structure.

An eleventh mode of the present invention provides the stent according to any of the first to tenth modes, wherein a weak part for which strength is made partially lower is formed in the skeleton by at least one of electroforming and etching.

With the stent constituted according to this mode, by providing the weak part in the skeleton, it is easier to realize things such as, for example, obtaining a stent shape that follows the lumen shape by being cut after placement, or forming a bifurcated opening part with a procedure that cuts and deforms when doing the placement disposition.

In particular, by the weak parts being formed by electroforming or etching, the troublesome operation of producing the weak part as a separate item from the other parts of the skeleton and adhering the weak part afterwards is not necessary, and it is possible to provide the weak part with a high level of dimensional precision. It is also possible to freely set the position and shape of the weak part, and to improve the level of the freedom of design.

A twelfth mode of the present invention provides the stent according to the eleventh mode, wherein the weak part has a smaller cross section area than that of other parts of the skeleton so as to be easily deformable.

With the stent constituted according to this mode, the weak part is for example formed thinner than the other parts of the skeleton, making it even easier to bend the stent, so that the weak part is cut with stability. In particular, when the weak part is formed by electroforming, for example, it is possible to make only the weak part thinner in the thickness direction, to change the material properties, or the like.

A thirteenth mode of the present invention provides the stent according to any of the first to twelfth modes, wherein a recess is provided on a surface of the skeleton.

With the stent constituted according to this mode, for example when formed by electroforming, it is possible to form the recess on the surface of the skeleton simultaneously with molding, or to provide a convex simultaneously with molding to provide the recess in relative form. Also, by using an uneven structure for the surface, for example, the performance of positioning on the surface of the lumen is improved, and it is also possible to hold a drug in the recess when placing the stent in the lumen. The recess of this mode can be formed on any surface, namely the inner circumference surface or the outer circumference surface of the peripheral wall made in a tubular shape. Also, the recess of this mode can be not only a shape having a bottom, but can also be a through hole formed by electroforming, etching or the like.

Also, with regard to the size of the recess according to this mode, the recess preferably has an opening dimension of about 10 to 30 µm, and by so doing, there is further reduction in the sense of a foreign object for the patient, and an adverse effect on the strength of the stent or the like is also avoided as practicably as possible.

A fourteenth mode of the present invention provides the stent according to any of the first to thirteenth modes, wherein the skeleton has a cross section shape for which a width dimension changes from an inner circumference surface thereof toward an outer circumference surface thereof.

With the stent constituted according to this mode, for example, the shape of the outer circumference surface of the stent peripheral wall that presses against the living body, the inner circumference surface of the stent peripheral wall that is exposed to blood flow or the like has an improved degree of freedom of design.

Effect of the Invention

With the invention according to claim 1, compared to the conventional stent having the simple rectangular cross section, there is a big increase in the degree of freedom of design. Therefore, it is possible to manufacture the stent according to the patient or according to the symptoms, for example.

In particular, with the invention according to claim 1, by using a roughly reverse triangle shape for the cross section shape of the stent skeleton, for example, it is possible to make the part that projects inside the lumen be smaller compared to the conventional stent having the simple rectangular cross section, and possible to inhibit turbulence of the fluid inside the lumen. Furthermore, when the stent is placed inside the blood vessel, the formation of clots which accompanies turbulence is avoided, and the risk of restenosis of the blood vessel at the location at which the stent is placed that accompanies adherence of the clot to the stent is reduced. Also, when the stent has the diameter reduced to be mounted in a delivery catheter or the like, it is possible to further reduce the diameter compared to conventional stents, and to increase deliverability.

Also, with the stent manufactured according to the invention of claim 5, when a heteromorphic shape is given by a skeleton formed with electroforming or etching, for example, it is possible to obtain the stent with a shape corresponding to the bifurcated part of the blood vessel or the like from the start, for example. Also, by having the stent shape correspond with good precision to a lumen such as a blood vessel or the like, the procedure is easy, and suitability to the living body is also improved, thereby reducing distortion and residual stress of the placed stent itself. Also, since the cutting part is less than that of the stent manufactured by conventional laser processing, it is possible to form the stent with better yield.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A shows a roughly triangular shape, and FIG. 4B shows a roughly reverse triangular shape.

FIGS. 5A-5C are views schematically showing positions of a weak part employable in the stent of the present invention.

FIG. 6 is a view schematically showing a preferable position of the weak part of the stent of the present invention.

FIG. 7 is a front view showing the overall shape of the molding state of the stent as a fourth embodiment of the present invention.

FIG. 8A is a perspective view showing an enlarged cross section in the axis-perpendicular direction of the stent shown in FIG. 7, and FIG. 8B is an enlarged view showing the major part of FIG. 8A viewed in the axial direction.

FIG. 16 is a view suitable for describing the major part of the stent shown in FIGS. 14A and 14B with its diameter reduced, corresponding to FIG. 10.

FIGS. 17A and 17B are views suitable for describing the major part of the stent shown in FIG. 16 with its diameter reduced, corresponding to FIGS. 11A and 11B.

FIG. 20A shows the speed distribution near the blood vessel wall surface with vectors, and FIG. 20B shows the speed distribution near the blood vessel wall surface with a surface.

EMBODIMENTS FOR CARRYING OUT THE INVENTION

Figure 1:
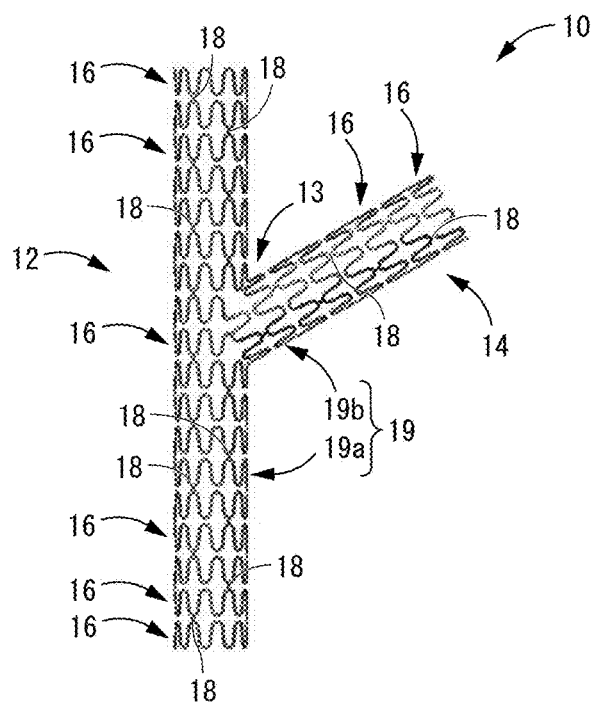
FIG. 1 is a front view showing the overall shape of a stent as a first embodiment of the present invention.

Following, we will describe embodiments of the present invention while referring to the drawings.

First, FIG. 1 shows the molding state of a stent 10 as a first embodiment of the present invention before contraction or expansion. This stent 10 is delivered to a stenosis portion of a body lumen such as a blood vessel or the like, and by placing the stent at this stenosis portion in an expanded state, the body lumen is maintained in an expanded state. With the description hereafter, the axial direction means the vertical direction in FIG. 1.

The stent 10 of this embodiment is equipped with a base tube part 12 and a bifurcated tube part 14 each extending in a straight line with a roughly round tubular shape, and has an overall roughly Y-shaped bifurcated shape by the bifurcated tube part 14 extending at an incline to the side from a bifurcation 13 provided at the middle part in the lengthwise direction of the base tube part 12. In other words, with the stent 10 of this embodiment, there is a different number of tube parts in the lengthwise direction (vertical direction in FIG. 1) by means of the bifurcation 13. Specifically, the stent 10 has a heteromorphic tubular shape whose cross section shape changes in the lengthwise direction.

A plurality of annular parts 16 for which curves or bends in a wave shape are repeated in the circumference direction and continuously extend are provided at a designated distance from each other in the axial direction on both the base tube part 12 and the bifurcated tube part 14. By so doing, a strut 19a in serial form that constitutes the base tube part 12 and a strut 19b in serial form that constitutes the bifurcated tube part 14 are respectively formed. Also, the annular parts 16, 16 adjacent in the axial direction of the struts 19a and 19b are linked by a link part 18 that extends in roughly the axial direction, thereby imparting a tube shape of a designated length.

In particular with this embodiment, with the bifurcated part, the annular part 16 that constitutes the base tube part 12 and the annular part 16 that constitutes the bifurcated tube part 14 extend continuously on the circumference of the base tube part 12 and the bifurcated tube part 14. By so doing, with the bifurcated part of the base tube part 12 and the bifurcated tube part 14, an integrated structure of the struts 19a and 19b is realized, constituting a single connected strut 19. Also, with this strut 19, the adjacent annular parts 16, 16 in the axial direction are linked by the link part 18, thus constituting the skeleton of the stent 10 of this embodiment. As a result, there is an improvement in the degree of freedom of strength and deformation for the stent 10, and local deformation such as buckling or the like of the strut 19 is prevented at the time of deformation.

The specific shape of the annular part 16 and the link part 18 is not limited with the present invention. The wave shape of the annular part 16, the linking portion by the link part 18, and the number of link parts 18 on the circumference of the annular part 16 or the like can be set as appropriate considering the required characteristics for the stent 10.

Also, the width dimensions and thickness dimensions of the annular part 16 and the link part 18 are not particularly limited. However, for the strut 19 constituting the annular part 16, from points such as ensuring strength, it is preferable to have the width dimension and thickness dimension of approximately 30 to 200 μm, and for the link part 18, it is preferable to have the width dimension and thickness dimension of approximately 10 to 100 μm.

Also, with this kind of bifurcated shape stent 10, each of the plurality of annular parts 16 and link parts 18 constituting the strut 19 is produced by being formed integrally using electroforming.

In specific terms, a molding base having the shape and size of the target base tube part 12 and the bifurcated tube part 14 is produced and prepared using a conductor such as stainless steel or the like. Also, on the surface of this molding base, an exposed surface is formed in a shape corresponding to each of the plurality of annular parts 16 and link parts 18, and a non-conductive mask is applied to the other areas. After that, the molding base is immersed in an electrolytic bath ionized with a designated metal, and metal ions are electrodeposited on the exposed surface of the molding base to perform electroforming. After obtaining metal of a designated thickness, the mask is removed, and by extracting or dissolving the molding base, it is possible to obtain the stent 10 of the target constitution as described above.

The stent 10 of this embodiment constituted as described above is expandable and contractible in the radial direction respectively with the base tube part 12 and the bifurcated tube part 14, and the diameter is reduced mechanically to a designated dimension from the state before contraction shown in FIG. 1. Also, during use, the stent 10 is delivered to the stenosis portion of a blood vessel, for example, by a delivery catheter or the like. After that, the stent 10 is expanded using a balloon catheter, or when the stent 10 is formed using a shape memory material, by the delivery catheter being released, the stent 10 expands automatically, and is placed in a body lumen such as a blood vessel in the state shown in FIG. 1.

Since the stent 10 of this embodiment is produced by electroforming, it is possible to integrally form the bifurcated shape having the base tube part 12 and the bifurcated tube part 14. Therefore, compared to when forming a bifurcated shape for which two stents obtained by laser processing of a straight, round tubular metal piece are connected in combination as with the conventional structure, it is possible to have less cutting part, making it possible to improve yield, and possible to obtain a complex bifurcated shape with good precision. Therefore, it is possible to realize the stent 10 corresponding with good precision to a complex shaped portion of a living body blood vessel or the like with good yield.

Also, the degree of freedom of design of the shape is significantly improved while ensuring integrated formability of the stent 10 by being produced using electroforming in this way. Thus, compared to the stent obtained by laser processing of a straight, round tubular metal piece of the conventional structure, it is possible to obtain stents having various types of heteromorphic initial shapes.

Figure 2:
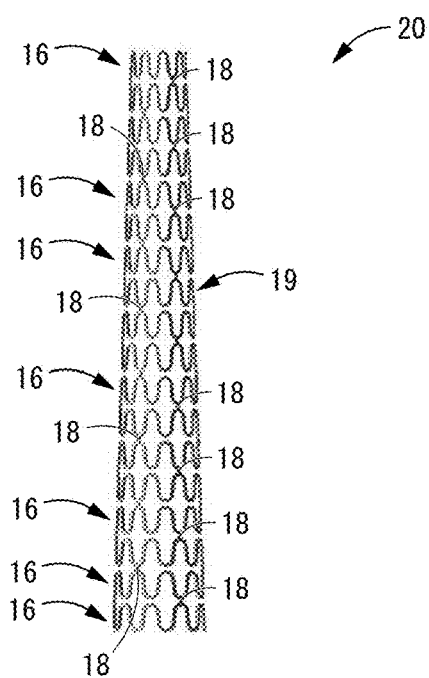
FIG. 2 is a front view showing the overall shape of a stent as a second embodiment of the present invention.

For example, as shown in FIG. 2, a stent 20 as a second embodiment of the present invention having a tapered tube shape for which the inner and outer diameter dimensions change in the axial direction can also be integrally formed by electroforming with an initial shape of the target taper angle. The stent 20 of this embodiment has this taper shape and is a heteromorphic tubular shape for which the cross section shape changes in the lengthwise direction. With the description hereafter, for the same parts and sites as those of the first embodiment, in the drawings, the same code numbers will be given as those of the first embodiment, and thus a detailed description will be omitted.

With this kind of stent 20, when placed in a blood vessel or the like for which the diameter dimension changes, the taper is given with the initial shape, so that it is possible to inhibit distortion and residual stress in the placed state.

Also, the skeleton of the stents 10 and 20 as described above, specifically, the strut 19 and the link part 18, are produced by electroforming, so that it is also possible to use a laminated structure of different materials. In specific terms, a non-conductive mask is formed on the surface of the molding base as described above, and after performing the first electroforming, by performing the second electroforming by electroforming in an electrolytic bath of a different metal ion, it is possible to form a metal layer of a different material by the second electroforming on the metal surface formed by the first electroforming.

This kind of metal laminated structure can be performed any number of times, and can have a structure for which a different metal can be provided covering a surface layer part so as to cover a core part formed with a specific metal, for example. At that time, for example, it is preferable that the ductility be greater for the metal of the surface layer part than for the metal of the core part. By so doing, the following capability when bending the stent is improved, and it is possible to avoid concentration of distortion or stress on the surface layer part.

Also, it is preferable that the ionization tendency of the metal of the surface layer part be smaller than the metal of the core part. In specific terms, for example while the core part is formed with stainless steel (SUS316L) or a CrCo alloy, tantalum, NiTi or the like, the surface layer part can be formed with Ni, NiCo, Cu, NiW, Pt, Au, Ag, Cr, Zn or the like, and particularly preferably with Au and Pt. By so doing, while efficiently ensuring the strength and rigidity of the metal constituting the core part, it is also possible to increase the biocompatibility by suppressing the difference in electric potential with the living body by the metal of the surface layer part. Also, since the ionization tendency is very low with Au, Pt and the like, it is possible to further inhibit metal elution. Yet further, it is also possible to suppress elution of metal ions that cause metal allergies such as Ni or the like used for the alloy that is the core material. In fact, since the specific gravity of Au, Pt and the like is large, and radiopaqueness is good, it is possible to improve visibility with stents using X-rays as well.

After the first electroforming is performed, it is possible to redo formation of the mask and perform the second electroforming. By so doing, it is possible to form the annular part 16 and the link part 18 with different metal materials, for example, and also possible to make the material of the annular part 16 partially different in the lengthwise direction or in the circumference direction of the stent 10.

Figure 3:
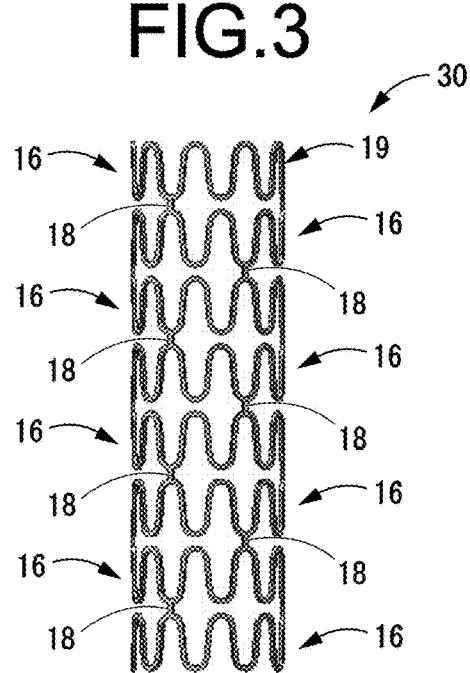
FIG. 3 is a front view showing the overall shape of a stent as a third embodiment of the present invention.

In specific terms, as shown in FIG. 3 as a third embodiment of the present invention, with a straight, round tubular shaped stent 30, by increasing the number of times of electroforming for one or a plurality of annular parts 16 positioned at the end part in the axial direction in comparison with that for the other annular parts 16 positioned at the center part in the axial direction, it is possible to make the axial end part thicker. Specifically, with the stent 30 of this embodiment, with a shape for which the thickness dimension changes in the lengthwise direction, the cross section shape changes in the lengthwise direction. By making the axial end part thicker than the center part, compared to the center part, the axial end part can have the outer diameter dimension be greater, or can have the inner diameter dimension be smaller, or can do both of these. Also, this thick part can be provided at one end part in the axial direction, or can be provided at both end parts in the axial direction.

In this way, with the heteromorphic tubular shaped stent 30 for which the end part in the axial direction is thicker than the center part, by the rigidity of the axial end part being greater than that of the center part, while ensuring a degree of freedom of deformation with the center part, it is possible to inhibit rising up of the axial end part from the blood vessel, and to prevent restenosis.

Also, after performing the first electroforming, by redoing the mask formation and performing the second electroforming, it is possible to form annular parts 16 skewed by a half pitch in the axial direction so as to cover the outer circumference straddling the adjacent annular parts 16, 16 positioned at the axial end part. Since it is also possible to reinforce the rigidity of the axial end part having this kind of complex structure, a high degree of freedom of design is realized.

With the stent 30 of this embodiment, at the axial end part for which the rigidity is made larger than that of the center part, it is preferable that the rigidity of the terminal part at the axial direction outside be roughly equal to or smaller than the center part. By so doing, it is possible to keep to a low level the load applied to the blood vessel wall of the axial direction terminal part of the stent placed so as to bite into the blood vessel wall. This terminal part with low rigidity can be realized, for example, by having only the terminal part formed with soft metal, or by adjusting the number of times for electroforming, the mask or the like, and so as to make the wall thickness dimension or width dimension of the terminal part be small.

Figure 4A:
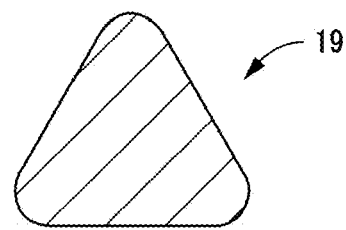
FIGS. 4A and 4B are cross section views showing specific examples of a skeleton that can be used with the stent of the present invention, where
Figure 4B:
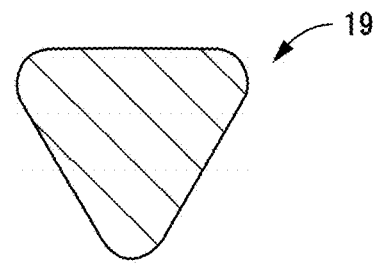

Furthermore, the stents 10, 20, and 30 as described above are produced by electroforming, so in terms of the freedom of design of the cross section shape of the strut 19 constituting the skeleton, a great degree of freedom is ensured in contrast to only having a simple rectangular cross section as with the laser processing of the conventional structure. For example, FIGS. 4A and 4B show the cross section shape of strut 19 for which the width dimension changes from the inner circumference surface toward the outer circumference surface. In FIGS. 4A and 4B, the top side is the side that abuts the blood vessel wall, and the lower side is the side positioned at the intravascular lumen.

In specific terms, as shown in FIG. 4A, it is possible to use the strut 19 for which the cross section is a roughly triangle shape. With this shape of strut 19, since the side abutting the blood vessel wall gradually becomes smaller, when the stent is expanded, it is possible to have the pressing force of the stent on the blood vessel wall concentrate on the tip part of the strut 19. By so doing, it is possible to expand the blood vessel with a smaller stent pressing pressure, in other words, the stent expansion pressure. Also, even when the blood vessel wall is hard such as with calcified lesions of the blood vessel or the like, the narrow tip part of the strut 19 eats into that, and a dividing action works on the calcified lesion part. Thus, it is possible to expand even blood vessels for which expansion was deemed to be difficult with the conventional rectangular cross section.

Also, as shown in FIG. 4B, it is also possible to use strut 19 for which the cross section is a roughly reverse triangle shape. With the strut 19 of that shape, the side positioned at the intravascular lumen gradually becomes narrower, so that the surface area in contact with the blood flow is smaller, and it is possible to suppress foreign matter reactions to the degree possible. Also, since stagnation does not occur easily for the flow of blood, it is possible to reduce the risk of the occurrence of clots and the like. Furthermore, since the surface area exposed to the intravascular lumen is small, it is possible to shorten the time until the strut 19 is covered by the vascular endothelial cells, and the strut 19 is embedded in the blood vessel quickly. Accordingly, it is possible to inhibit hypertrophy of the vascular endothelium, and the part at which the stent is placed can be healed in a relatively short time.

The strut 19 of this shape can be formed by arranging the shape of the mask in a desired shape when doing electroforming by etching or the like, and it is possible to greatly improve the freedom of design of the cross section shape. Naturally, the cross section shape of the strut 19 is not limited to the roughly triangular shape or the roughly reverse triangular shape shown in FIGS. 4A and 4B, and for example it is possible to use a semicircular shape, a double-tapered shape, or the like.

Furthermore, since the stents 10, 20, and 30 as described above are produced by electroforming, degree of freedom of the cross section shape of the link part 18 that links the annular parts 16, 16, and thus the strength and weakness level thereof can be greatly ensured. In this way, by providing low strength portions partially on the stent skeleton, the weak portions during bending of the expanded stent are easily deformed and cut, and it is easier for the stent to follow the shape of the body lumen. Also, even when an opening part is formed on the stent in response to a bifurcated blood vessel or the like, it is possible for the operation of cutting, pressing and expanding the weak portions to be performed easily by the practitioner.

Here, with the stents 10, 20, and 30, with the skeleton, by means of the link part 18, a weak part is constituted for which the strength is lower than that of the annular part 16. By producing the link part 18 using electroforming, compared to being able to form a narrow shape only for the width direction of the strut 19 with the laser processing of the conventional structure, it is possible to form not only this narrow shape in the width direction, but also a thin shape in the thickness direction of the strut 19. The cross section shape of the link part 18 can also be formed in a shape other than a rectangle in contrast to only being able to use a simple rectangular cross section with conventional laser processing.

In specific terms, for example as shown in FIGS. 5A-5C, it is possible to change the design as appropriate for the position of the link part 18 in the thickness direction in relation to the annular parts 16, 16. In FIGS. 5A-5C, the upper part shows the blood vessel wall side, and the lower part shows the intravascular lumen side. Specifically, with FIG. 5A, while the annular parts 16, 16 are linked by the link part 18 at the blood vessel wall side, with FIG. 5B, the annular parts 16, 16 are linked by the link part 18 at the center part in the thickness direction. Also, with FIG. 5C, the annular parts 16, 16 are linked by the link part 18 on the intravascular lumen side. Furthermore, the link parts 18 positioned at the blood vessel wall side, center part, and intravascular lumen side can also be combined. With FIGS. 5A-5C, the strut 19 and the link part 18 are shown with rectangular cross sections, but FIGS. 5A-5C simply show the relative positions of the annular parts 16, 16 and the link part 18, and there is no limitation whatsoever on the shape of the strut 19 and the link part 18.

In this way, with conventional laser processing, one pipe is pierced in the thickness direction, so it was only possible to form the annular part and the link part with the same thickness. On the contrary, by manufacturing the stents 10, 20, and 30 using electroforming, the thickness dimension of the link part 18 can be made thinner. By so doing, it is possible to form the link part 18 to be thin and narrow, and when cutting the link part 18, it is even easier to cut than in the past. Also, in the past, a post-adhesion method was also used wherein the annular part 16 and the link part 18 were formed as separate units, but by manufacturing stents 10, 20, and 30 using electroforming, the annular part 16 and the link part 18 are integrally formed, and it is possible to do manufacturing easily while ensuring a high degree of dimensional precision. Furthermore, since the cutting surface of the link part 18 is made smaller, it is possible to inhibit to as much a degree as possible the irritation caused by the cutting surface contacting the blood vessel wall and the like.

Furthermore, the position of the link part 18 can have its design changed as appropriate for the width direction of the strut 19 as well. Whereas it is also possible to form the link part 18 at the widthwise end part in relation to the strut 19, the link part 18 is preferably formed at the widthwise center part of the strut 19, as shown in FIG. 6, specifically, with the embodiments described previously, at the widthwise center part of the bent part of the annular part 16. In particular, the link part 18, as shown in FIG. 6, is preferably positioned at the center part of the strut 19 in the thickness direction as well. By so doing, it is possible to further reduce the risk of the cutting surface of the link part 18 contacting the blood vessel wall, and to further reduce the discomfort given to the patient.

In FIG. 6 as well, the strut 19 and the link part 18 are shown with a rectangular cross section, but FIG. 6 simply shows the relative position of the annular part 16 and the link part 18, and there is no restriction whatsoever on the shape of the strut 19 and the link part 18.

Next, FIGS. 7, 8A and 8B show a stent 32 as a fourth embodiment of the present invention. This stent 32 overall has a roughly round tubular shape and extends in a straight line.

Here, the cross section shape of the strut 19 with the stent 32 of this embodiment is formed as a heteromorphic structure that differs in the thickness direction (vertical direction in FIG. 4B) as shown in FIG. 4B, and the width dimension (lateral direction dimension in FIG. 4B) becomes larger from the inner circumference surface toward the outer circumference surface.

Specifically, with this embodiment, the cross section shape of the strut 19 is roughly a reverse triangle. Also, with this embodiment, by implementing chamfering such as sandblasting, chemical polishing, electrolytic polishing or the like on the edge part of the reverse trapezoid cross section shape shown in FIG. 8B, the roughly reverse triangle cross section shape shown in FIG. 4B is formed. With the cross section shape before chamfering shown in FIG. 8B, if the width dimension of the outer circumference surface is W, it is preferable to set such that 60 mm≤W≤180 mm, and even more preferable to set such that 80 mm≤W≤130 mm, and with this embodiment, it is set such that W=125 mm.

Figure 9:
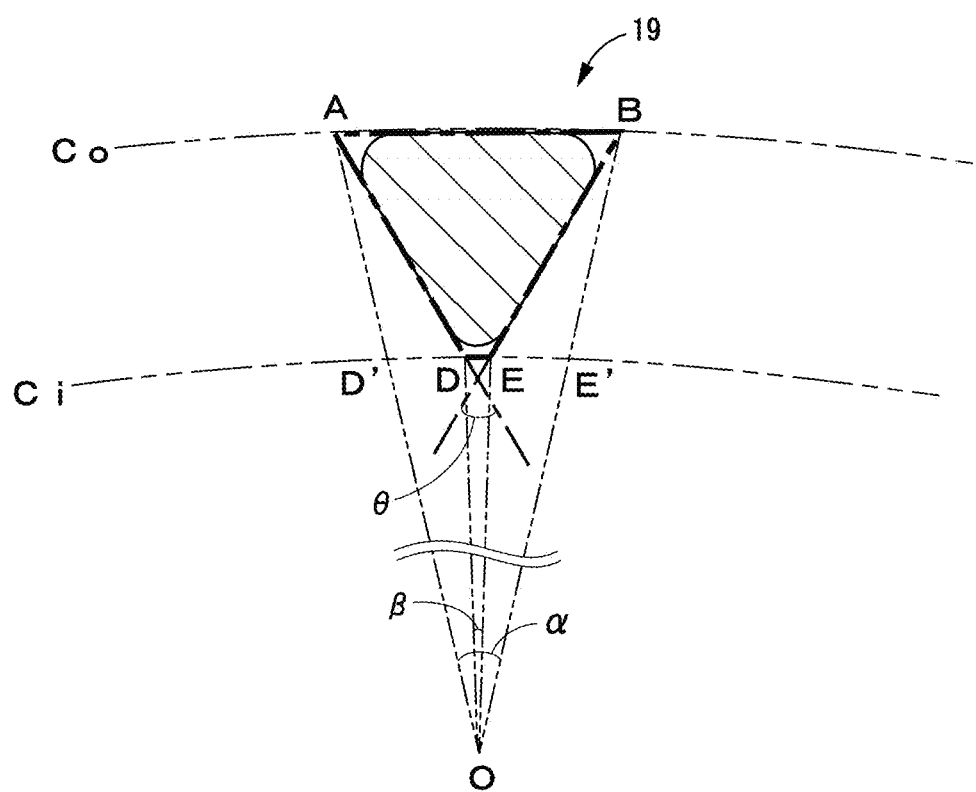
FIG. 9 is a view suitable for describing the sizes of the central angle of the outer circumference surface and the included angle of both side surfaces in the circumference direction with the cross section view of the skeleton shown in FIG. 4B.

Therefore, with this embodiment, as shown in FIG. 9, compared to the central angle α of the arc of the outer circumference surface of the strut 19, the central angle β of the arc of the inner circumference surface is smaller (β<α). Specifically, in relation to two points A and B of the outer circumference surface for which the width dimension is greatest with the cross section shape (bold dot-and-dash line in FIG. 9) of strut 19 before chamfering processing, we assume an arc Co that is convex to the outer circumference side passing through these points A and B and a curvature center O positioned further to the inner circumference side than the strut 19 as the curvature center of the arc Co. Also, we assume an arc Ci with point O as the curvature center with the cross section shape of the strut 19 before chamfering processing, and the two points of the inner circumference surface of the strut 19 for which the width dimension is smallest and which are positioned on that arc Ci are assumed to be D and E. Here, if ∠AOB is the central angle α of the arc of the outer circumference surface of the strut 19, and ∠DOE is the central angle β of the arc of the inner circumference surface of the strut 19, with the strut 19, the central angle β is smaller than the central angle α.

Also, with this embodiment, compared to the central angle α of the arc of the outer circumference surface of the strut 19, the included angle θ of both side surfaces is larger (α<θ). This included angle θ is formed by the straight line AD and the straight line BE in FIG. 9 intersecting in the cross section shape of the strut 19 before chamfering processing.

The central angle α of the outer circumference surface is preferably set to be within a range of 1°≤α≤45°, and more preferably 4°≤α≤15°. Meanwhile, the central angle β of the inner circumference surface is preferably set within a range of 0°≤β≤30°, and more preferably 0°≤β≤10°. Also, the included angle θ of both side surfaces is preferably set within a range of 15°≤θ≤150°, and more preferably 30°≤θ≤100°. By setting the respective central angles α and β of the outer circumference surface and the inner circumference surface, and the included angle θ of both side surfaces to within the ranges noted above, it is possible to stably exhibit the fluid turbulence prevention effect and the outer diameter reduction effect during diameter reduction described later.

With the stent 32 of this embodiment with this shape, the strut 19 and each link part 18 which are the skeleton are produced to be a metal skeleton integrally formed by electroforming.

Figure 10:
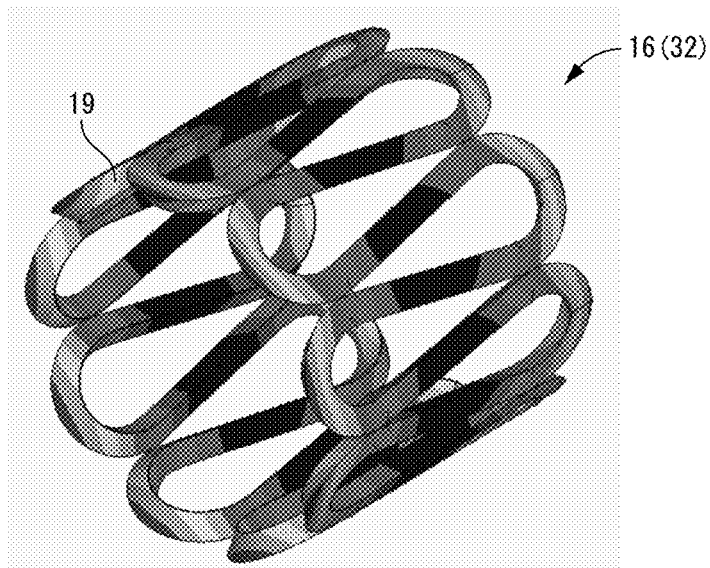
FIG. 10 is a view suitable for describing the major part of the stent shown in FIG. 7 with its diameter reduced.
Figures 11A, 11B:
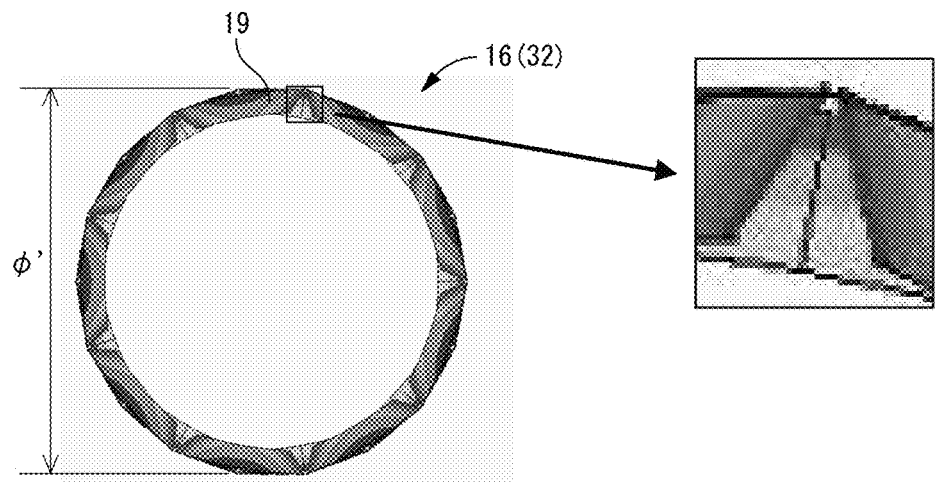
FIG. 11A is a view of the stent shown in FIG. 10 viewed in the axial direction with its diameter reduced.
FIG. 11B is an enlarged view showing the major part of FIG. 11A.

The stent 32 of this embodiment is expandable and contractible in the radial direction, and with the diameter reduced mechanically to a designated dimension from the state before contraction shown in FIG. 7, the stent 32 is led to the diameter reduced state shown in FIGS. 10, 11A and 11B. Note that FIG. 10 shows one of the annular parts 16 constituting the stent 32, and the other annular parts 16 and the link part 18 connecting the annular parts 16, 16 are omitted from the drawing.

Here, as shown in FIG. 4B, the cross section shape of the strut 19 has a roughly reverse triangle shape, and by having a reduced diameter state, at both end parts in the axial direction of the annular part 16, the adjacent parts in the circumference direction of the strut 19 abut each other. At that time, as shown in FIG. 11B, by having the circumference end parts of the outer circumference side abut each other with the cross section shape of the strut 19, the diameter reduction of the stent 32 is limited, and the outer diameter dimension of the stent 32 in the diameter reduced state is regulated.

With the stent 32 of this embodiment constituted as noted above, since the cross section shape of the strut 19 is a roughly reverse triangle, compared to the stent for which the skeleton has a rectangular cross section of the conventional structure, for example, it is possible to make the part exposed to blood flow on the inner circumference side of the stent 32 smaller. By so doing, obstruction of the flow of blood by the stent 32 is inhibited, and it is possible to prevent the blood flow from becoming sluggish or becoming turbulent (turbulence) in connection with placing of the stent 32 within the blood vessel. Therefore, formation of a clot in the blood vessel or within the heart due to turbulence is inhibited, and it is possible to effectively prevent restenosis at the position at which the stent 32 is placed due to adhering of the clot to the stent 32.

Also, since the surface area exposed from the blood vessel wall is small, embedding in the vascular endothelial cell occurs early. Specifically, healing can be done in a relatively short time with the blood vessel wall for which a crack has occurred along with placement of the stent 32. Thus, hypertrophy of the vascular endothelial cell is inhibited, and it is possible to avoid restenosis at the position at which the stent 32 is placed for which a clot has adhered to a hypertrophied vascular endothelial cell. Naturally, even if there is hypertrophy of the vascular endothelial cell, since many gaps are formed at the inner circumference side of the stent 32, vascular endothelial cells enter those gaps, so that growth of the vascular endothelial cells to the inner circumference side is inhibited, thereby further reducing of the risk of restenosis at the position at which the stent 32 is placed.

Yet further, with the stent for which the skeleton has the rectangular cross section of the conventional structure, during diameter reduction, the corner of the inner circumference side at the skeleton cross section is quickly abutted, and further diameter reduction is limited. However, with the stent 32 of this embodiment, since the cross section shape of the strut 19 has a roughly reverse triangle shape, abutment will not occur at the inner circumference side but will occur at the outer circumference side of the strut 19. By so doing, the stent 32 of this embodiment has even less limitation on the diameter reduction than the stent of the conventional structure, and it is possible to make the outer diameter dimension during diameter reduction even smaller. In particular, as shown with this embodiment, by having the included angle θ of both side surfaces be greater than the central angle α of the outer circumference surface, the risk of abutting at the inner circumference side will be further reduced, thereby reliably making the outer diameter dimension smaller during diameter reduction. As a result, it is possible to improve the deliverability of the stent 32 and the delivery catheter to which the stent 32 is mounted.

Figure 12:
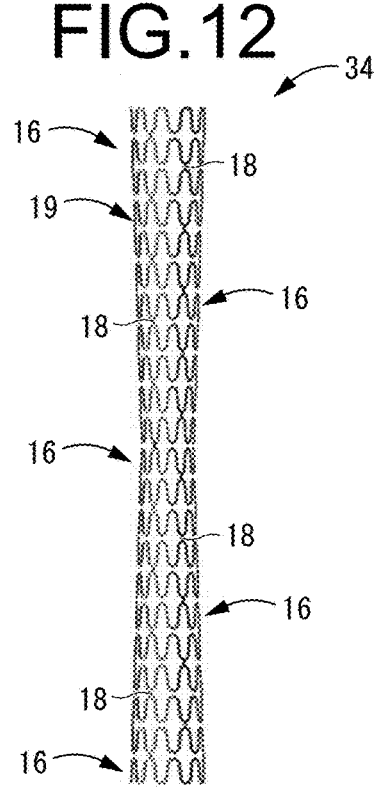
FIG. 12 is a front view showing the overall shape of the stent as a fifth embodiment of the present invention.

Next, FIG. 12 shows a stent 34 as a fifth embodiment of the present invention. The stent 34 of this embodiment has a skeleton structure comprising the strut 19 and the link parts 18 the same as with the fourth embodiment, and the cross section shape of the strut 19 also has the shape shown in FIG. 4B, the same as with the fourth embodiment.

The stent 34 of this embodiment has a heteromorphic tubular shape for which the outer diameter dimension at both end parts in the axial direction (vertical direction in FIG. 12) is greater than the outer diameter dimension at the axial center part. The stent 34 of this embodiment, in contrast to the straight, round tubular shaped stent 32 shown in FIG. 7, for example, can be formed by performing a larger number of times of electroforming on the plurality of annular parts 16 positioned at both end parts in the axial direction to make them thicker than on the annular parts 16 positioned at the axial center part. Specifically, the stent 34 of this embodiment preferably has a laminated structure comprising a plurality of types of metal. This laminated structure does not have to be used across the entire stent, and can be used on specific parts of the stent. Also, the shape of the inner hole of the stent 34 is not limited whatsoever, and can be a straight shape extending in the axial direction, or can have a larger diameter for both end parts than for the axial center part, for example.

Furthermore, the stent 34 of this embodiment, by being made thicker at both end parts in the axial direction than at the axial center part, the rigidity of both end parts is greater than that of the center part.

With the stent 34 of this embodiment having the shape as described above as well, since the cross section shape of the skeleton is the same shape as that of the fourth embodiment, the same effects are exhibited as with the fourth embodiment. In addition to that, with this embodiment, both end parts in the axial direction have a larger outer diameter dimension than the axial center part, and the rigidity is made greater. Accordingly, rising up of both ends in the axial direction of the stent 34 from the blood vessel is inhibited, and it can be placed stably at the stenosis portion of the blood vessel. In particular, if the axial end parts of the stent placed inside the blood vessel become separated from the blood vessel, the risk of formation of clots caused by blood vessel turbulence will increase. Therefore, as with this embodiment, by suppressing rising up of both end parts in the axial direction of the stent 34 from the blood vessel, it is possible to more effectively prevent restenosis at the position at which the stent is placed. Furthermore, by making the rigidity of the axial terminal part smaller, the load applied to the blood vessel wall can be kept small for the axial terminal part of the stent placed so as to bite therein.

Figure 13:
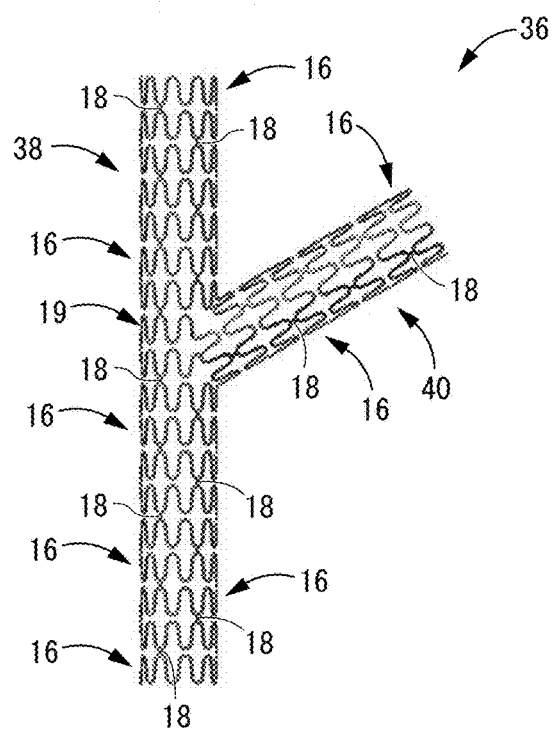
FIG. 13 is a front view showing the overall shape of the stent as a sixth embodiment of the present invention.

Next, FIG. 13 shows a stent 36 as a sixth embodiment of the present invention. The stent 36 of this embodiment, the same as with the first embodiment, has a roughly Y-shaped skeleton structure comprising the strut 19 and the link part 18, and the cross section shape of the strut 19 has a shape as shown in FIG. 4B, the same as with the fourth embodiment.

With the stent 36 of this embodiment, a base tube part 38 and a bifurcated tube part 40 formed as separate units can be connected together by a means such as adhesion or the like, but it is also possible to have the base tube part 38 and the bifurcated tube part 40 be integrally formed by electroforming.

Owing to the stent 36 of this embodiment having this shape as well, since the cross section shape of the strut 19 is the same shape as that of the fourth embodiment, it is possible to exhibit the same effects as those of the stent 32 of the fourth embodiment. In particular, the stent 36 of this embodiment is able to correspond to a complex shape such as of a blood vessel of a living body having a bifurcated shape, and by inhibiting turbulence of the blood flow even at the bifurcated part of the blood vessel, it is possible to more effectively prohibit restenosis of the blood vessel.

EXAMPLES

Figure 14A:
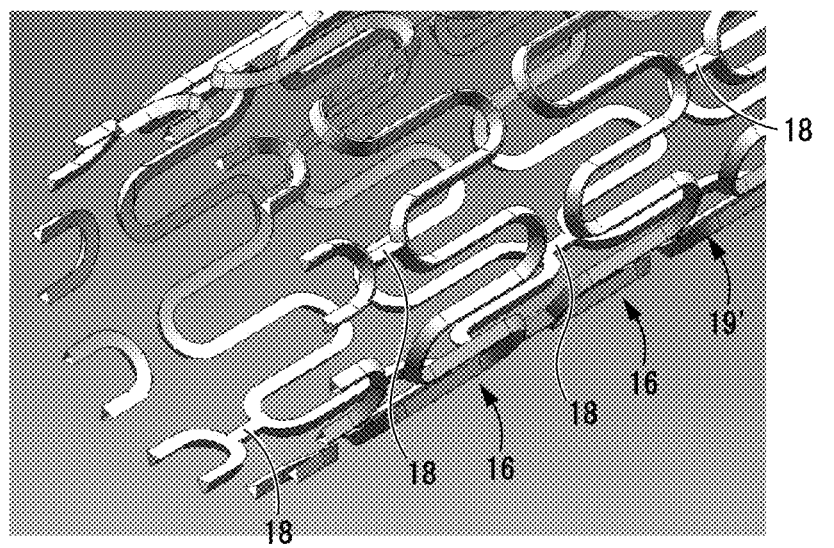
FIGS. 14A and 14B are views suitable for describing a stent as Example of the present invention, corresponding to FIGS. 8A and 8B.
Figure 14B:
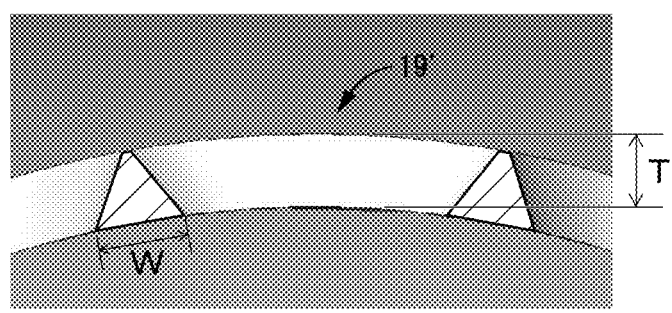
Figure 15A:
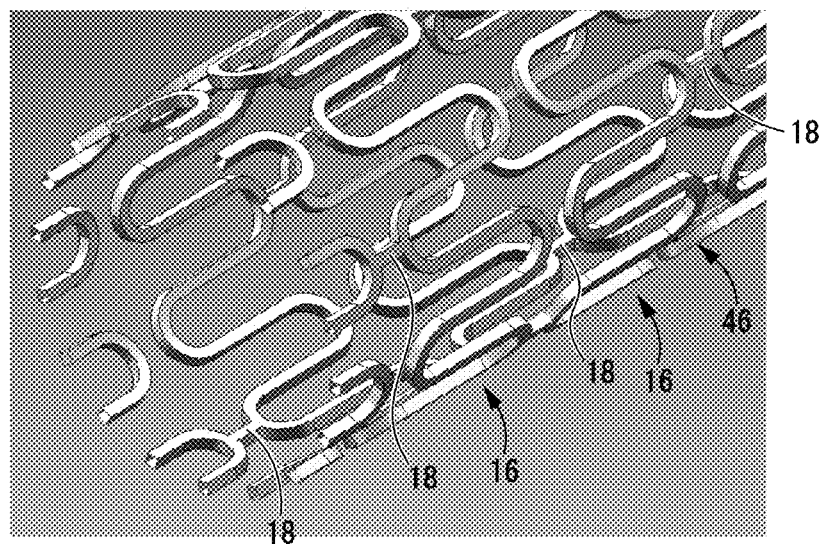
FIGS. 15A and 15B are views suitable for describing a stent as Comparative Example of the present invention, corresponding to FIGS. 8A and 8B.
Figure 15B:
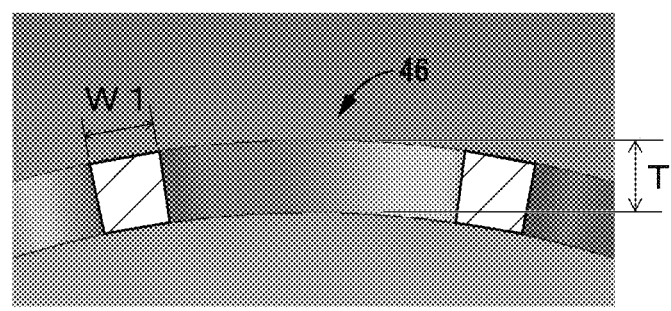
Figure 18:
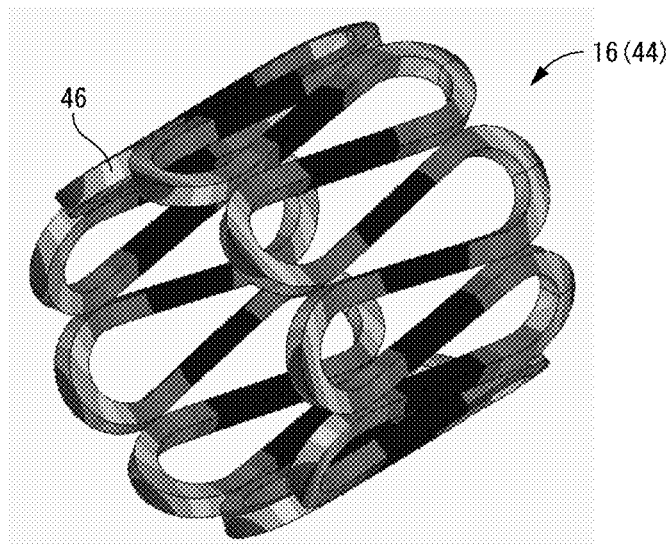
FIG. 18 is a view suitable for describing the major part of the stent shown in FIGS. 15A and 15B with its diameter reduced, corresponding to FIG. 10.

As Example 1 of the present invention, the stent 32 constituted according to the fourth embodiment shown in FIGS. 7, 8A and 8B was virtually produced on a computer. Also, as Example 2 of the present invention, as shown in FIGS. 14A and 14B, a stent 42 was used for which the cross section shape of the skeleton has the width dimension which becomes smaller from the inner circumference surface toward the outer circumference surface so as to have a roughly triangular shape, and as Comparative Example of the present invention, as shown in FIGS. 15A and 15B, a stent 44 with a rectangular cross section of the conventional structure was used, and those were both produced virtually on the computer. The stents 42 and 44 of Example 2 and Comparative Example respectively shown in FIGS. 14A/14B and 15A/15B show items in the molding state before diameter reduction, and the stents 32, 42, and 44 of Examples 1, 2, and Comparative Example were produced assuming the items before performing chamfering processing on the respective edge parts.

Also, the outer diameter dimensions of stents 32, 42, and 44 of the Examples 1, 2, and Comparative Example before diameter reduction were all set to =3 mm (see FIG. 7). Furthermore, while the width dimension of the outer circumference surface of the cross section of the strut 19 with Example 1 was W=125 mm (see FIG. 8B), the width dimension of the inner circumference surface of the cross section of a strut 19' with Example 2 was also W (see FIG. 14B). Furthermore, the width dimension of the outer circumference surface of the cross section of a strut 46 with Comparative Example was W1=100 mm (see FIG. 15B). Also, the thickness dimensions of the struts 19, 19', and 46 of Examples 1, 2, and Comparative Example were all set to the same, namely T=0.1 mm (see FIG. 8B).

Then, diameter reduction processing was implemented on the stents 32, 42, and 44 of Examples 1, 2 and Comparative Example produced virtually on a computer, and the respective outer diameter dimensions were compared. FIGS. 10, 11A and 11B described previously show a perspective view and views seen in the axial direction of the annular part 16 for which diameter reduction processing was implemented on the stent 32 of Example 1, and FIGS. 16-19B show perspective views and views seen in the axial direction of the annular part 16 for which diameter reduction processing was implemented on the stents 42 and 44 of Example 2 and Comparative Example. In this way, the respective outer diameter dimensions of stents 32, 42, and 44 of Examples 1, 2 and Comparative Example for which diameter reduction was implemented were compared as ø' (see FIG. 11A), ø1 (see FIG. 17A), and ø2 (see FIG. 19A). As software for implementing this diameter reduction processing and doing analysis, ANSYS R14.5 made by ANSYS, Inc. was used.

As a result, ø'=1.68 mm in comparison to ø1=1.80 mm and ø2=1.70 mm. Specifically, it was demonstrated that with the stent 32 for which the cross section shape of the strut 19 is a roughly reverse triangle shape, the outer diameter dimension when diameter reduction processing has been implemented was smaller than with the stent 42 for which the cross section shape of the strut 19' is a roughly triangular shape and the stent 44 for which the cross section shape of the strut 46, which is the conventional structure, is rectangular.

Figure 19A:
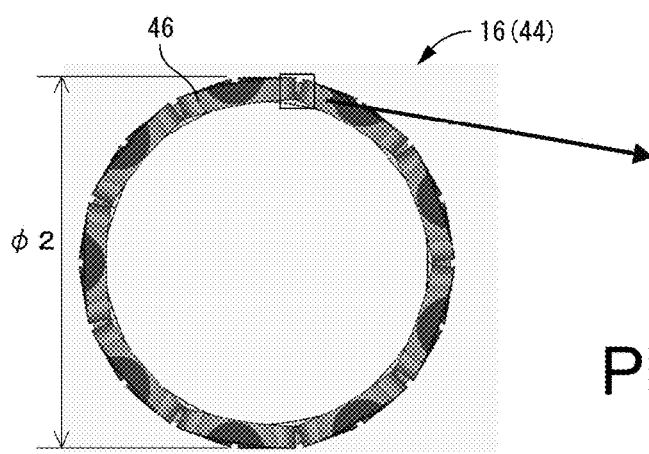
FIGS. 19A and 19B are views suitable for describing the major part of the stent shown in FIG. 18 with its diameter reduced, corresponding to FIGS. 11A and 11B.
Figure 19B:
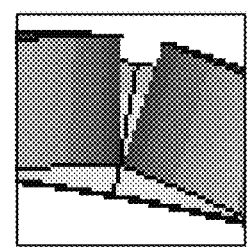

As a reason for the outer diameter dimension of the stent 32 of Example 1 being smaller than that of the stent 42 of Example 2 and the stent 44 of Comparative Example after diameter reduction processing, with the stent 42 and 44 of Example 2 and Comparative Example, as shown in FIG. 17B and FIG. 19B, when diameter reduction is implemented, the circumferentially adjacent inner circumference sides of the skeleton quickly abut each other, and further diameter reduction is restricted. On the other hand, as shown in FIG. 11B, the stent 32 of Example 1 has the width dimension of the inner circumference surface made smaller than the width dimension of the outer circumference surface. Thus, diameter reduction is not restricted until the circumferentially adjacent outer circumference sides of the skeleton abut each other, and it is conjectured that the outer diameter dimension will become even smaller.

By so doing, the stent 32 of Example 1 can have its outer diameter dimension during diameter reduction be smaller than that of the stent 42 of the roughly triangular cross section of Example 2 or the stent 44 of the rectangular cross section which is the conventional structure. Accordingly, it is also possible to make the outer diameter dimension smaller during mounting of a delivery catheter, thereby exhibiting good deliverability.

Figure 20A:
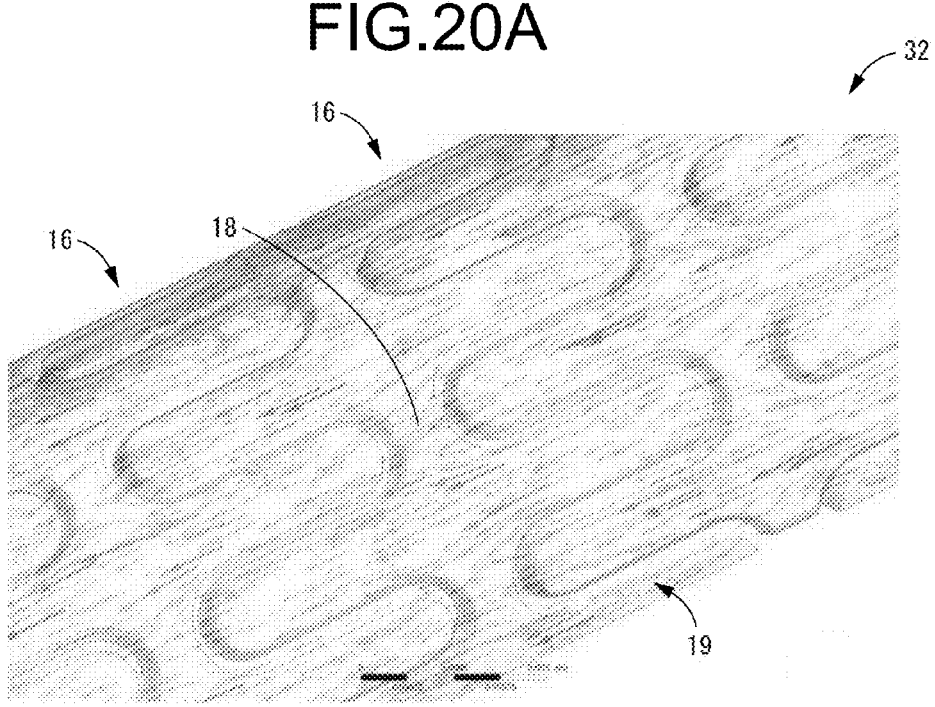
FIGS. 20A and 20B are views suitable for describing the results of confirming the flow speed using the stent shown in FIG. 7 as Example of the present invention, where
Figure 20B:
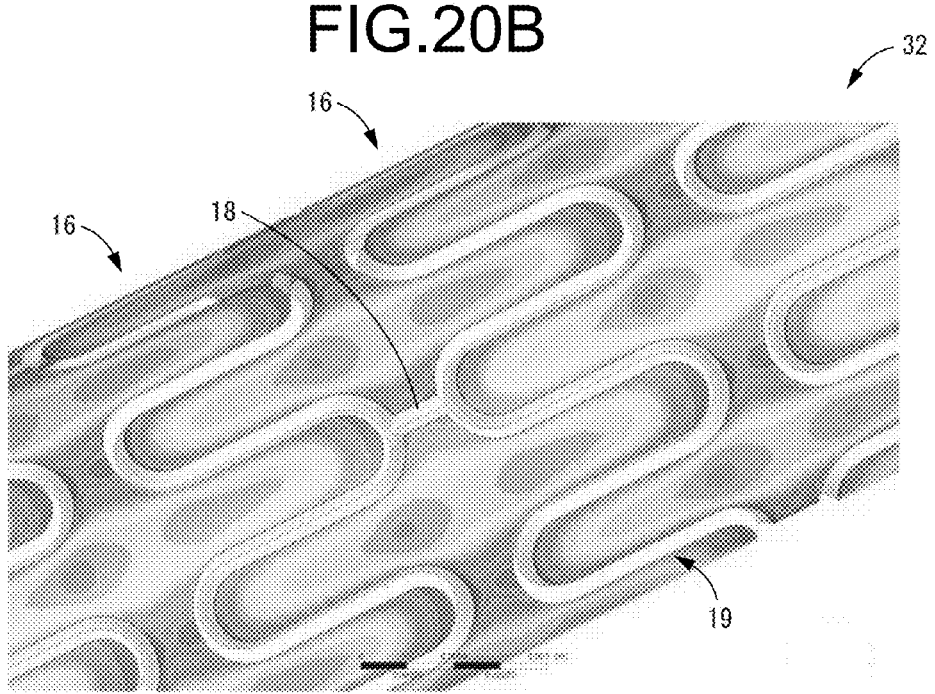
Figure 21A:
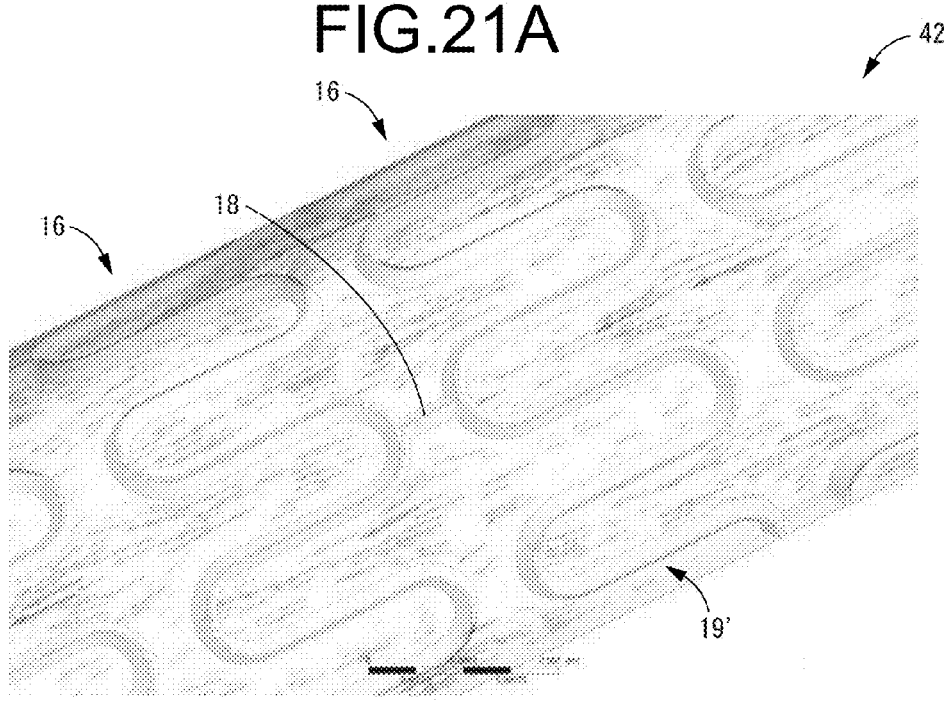
FIGS. 21A and 21B are views suitable for describing the results of confirming the flow speed using the stent shown in FIGS. 14A and 14B as another Example of the present invention, corresponding to FIGS. 20A and 20B.
Figure 21B:
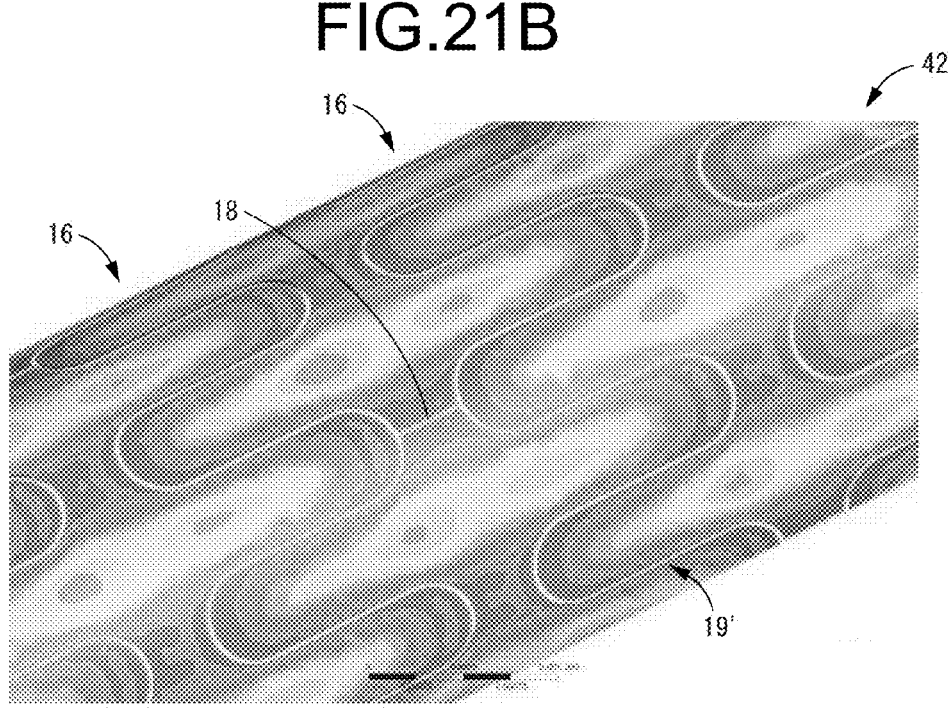
Figure 22A:
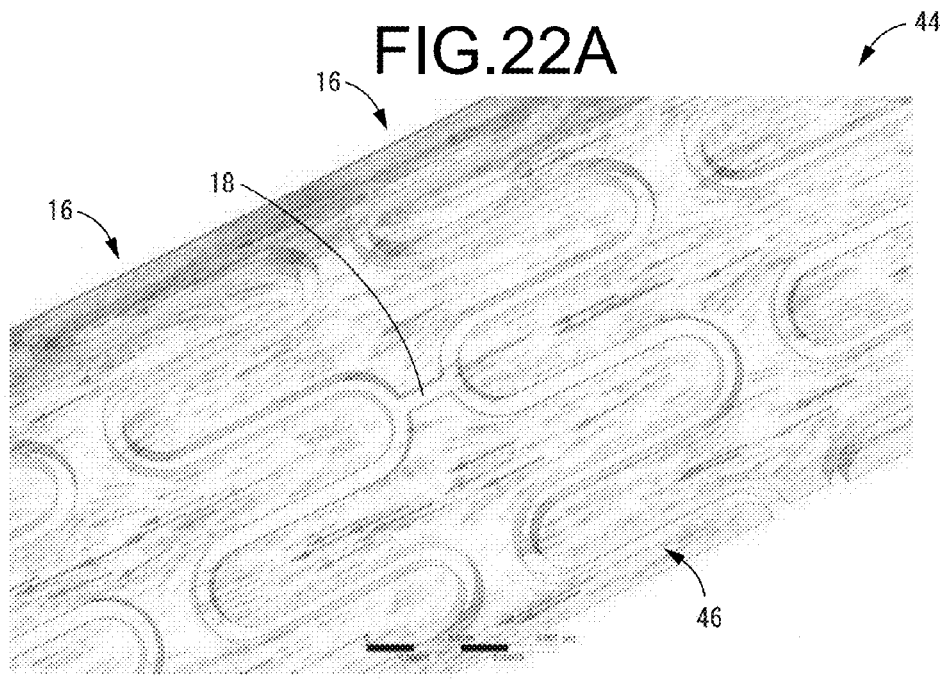
FIGS. 22A and 22B are views suitable for describing the results of confirming the flow speed using the stent shown in FIGS. 15A and 15B as Comparative Example of the present invention, corresponding to FIGS. 20A and 20B.
Figure 22B:
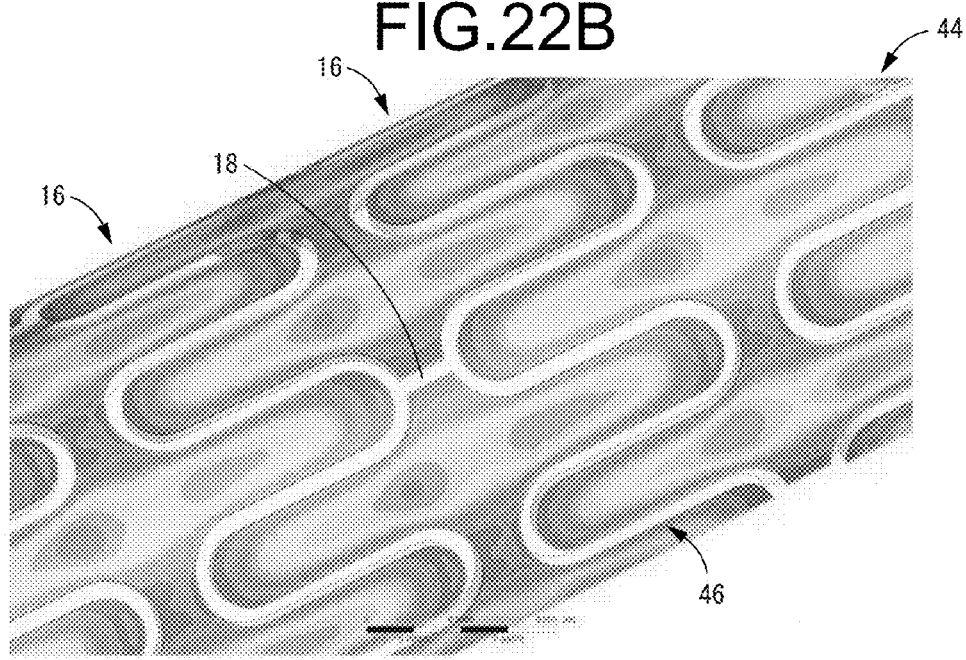

Also, using the aforementioned stents 32, 42, and 44 of Examples 1, 2, and Comparative Example, the flow speed near the respective struts was confirmed. The results for Examples 1 and 2 are shown respectively in FIGS. 20A/20B and 21A/21B, and the results for Comparative Example are shown in FIGS. 22A and 22B. The stents 32, 42, and 44 shown in FIGS. 20A-22B are items in the molding state respectively shown in FIGS. 8A/8B, 14A/14B, and 15A/15B, and their respective outer diameter dimensions were all set to ø=3 mm. Also, FIGS. 20A, 21A, and 22A show the speed distribution near the blood vessel wall surface with vectors, and furthermore, FIGS. 20B, 21B, and 22B show the speed distribution near the blood vessel wall surface with the surface. With FIGS. 20A-22B, the analysis results output and displayed with a colored image are difficult to see because it is shown in gray scale for the patent application. In fact, at the dark gray colored part in the drawing, the flow is indicated as being fast, while at the light colored part, the speed is shown as being slow, and step-like changes in the flow speed are shown corresponding to changes from the dark gray part to the light colored part. This analysis was implemented using the ANSYS R14.5 software made by ANSYS, Inc.

As a result of comparing FIGS. 20A-22B, compared to FIGS. 21A and 22A, FIG. 20A shows larger or a higher number of dark gray vector lines indicating fast flow overall. The reason why the quantity of vector lines is smaller in FIGS. 21A and 22A is that because the line color is light and the flow is slow, the vector lines are not displayed to be large, or there is almost no flow itself, so it looks as if there are no vector lines. On the other hand, compared to FIGS. 21B and 22B, FIG. 20B shows many parts for which the color is lit dark overall. Accordingly, it was demonstrated that the speed of the fluid that passes through near the strut of the stent 32 of Example 1 was faster than the flow speed of the fluid passing through near the strut of the stent 42 of Example 2 and stent 44 of Comparative Example. As a result, with the stent 32 of Example 1, in contrast to the stent 42 of Example 2 and the stent 44 of Comparative Example, the fluid is allowed to flow without stagnation at the position where the stent is placed within the lumen. In particular, when the stent 32 is placed in a blood vessel, it is suggested that it is possible to exhibit to an even greater degree the effect of preventing restenosis at the position where the stent is placed that accompanies the occurrence of clots due to blood stagnation or turbulence, and the adherence to that clot to the stent.

As the reason for exhibiting this effect, since the cross section of the strut 19 of the stent 32 of Example 1 is a roughly reverse triangle, compared to the roughly triangular cross section strut 19' as shown with Example 2 or to the rectangular cross section strut 46 as shown with Comparative Example, it is possible to make the part that projects to the inner circumference side smaller, and it is conjectured that obstruction of the flow of fluid passing through the interior of the stent 32 is inhibited to the extent possible.

With the stent 42 of Example 2 noted above, the cross section shape of the strut 19' is roughly triangular, and the inner circumference sides of the strut abut each other relatively early. Thus, with the stent 42 of Example 2, there is the risk of the outer diameter contraction effect during diameter reduction not being sufficiently obtained. Also, when the stent 42 is placed inside the lumen, the part projecting from the lumen wall to the inner circumference side is relatively large, and that projecting part becomes a barrier to the fluid. This poses the risk that smooth flow of the fluid will be obstructed.

However, the outer circumference side has a narrow tip shape with the cross section shape of the strut 19', and by the narrow tip end of the stent 42 being placed so as to eat into the lumen wall, it is possible to effectively exhibit the positioning effect of the stent 42 within the lumen. In particular, even when the blood vessel wall hardens such as with calcified lesions and it is difficult for a stent with the conventional structure skeleton having a rectangular cross section to expand the blood vessel, the strut 19' has an effect of dividing the lesion portion by the narrow tip part of the outer circumference side thereof. Thus, even with a blood vessel for which expansion was difficult with the conventional rectangular cross section, as shown with Example 2 noted above, expansion is possible by using the stent 42.

Therefore, depending on the state of the patient or lesion portion, it is also possible to preferably use a stent for which the skeleton cross section shape is roughly a triangle. In this way, it is possible to manufacture stents with a large degree of freedom of design corresponding to the state of the stenosis portion or to the portion at which stenosis occurs. This also shows that the stents 32, 34, 36, and 42 of the present invention have excellent technical significance.

Above, we gave a detailed description of embodiments and examples of the present invention, but the present invention is not limited to those specific descriptions, and can be implemented in modes for which various modifications, corrections and improvements have been added based on the knowledge of a person skilled in the art, and those kinds of modes are also included in the scope of the present invention as long as they do not stray from the gist of the present invention.

For example, it is also possible to add a suitable shape such as embossing or the like on the surface of the stent. When the stent is produced by electroforming, by suitably setting the molding base, mask shape or the like used for electroforming, it is possible to easily transfer the suitable shape such as embossing or the like onto the surface. In this way, by giving dents and bumps on the outer circumference surface of the stent, for example it is possible to effectively use this as a drug eluting stent. Specifically, for example, by coating or covering a drug that suppresses cell proliferation on the outer circumference surface of the stent given the dents and bumps, or a resin layer that contains that drug, it is possible to elute that drug to the blood vessel wall. At that time, the wettability is improved by the dents and bumps, and it is easier for the coated or covered drug or resin layer to adhere to the stent outer circumference surface, while it is difficult for them to peel off.

Figure 23:
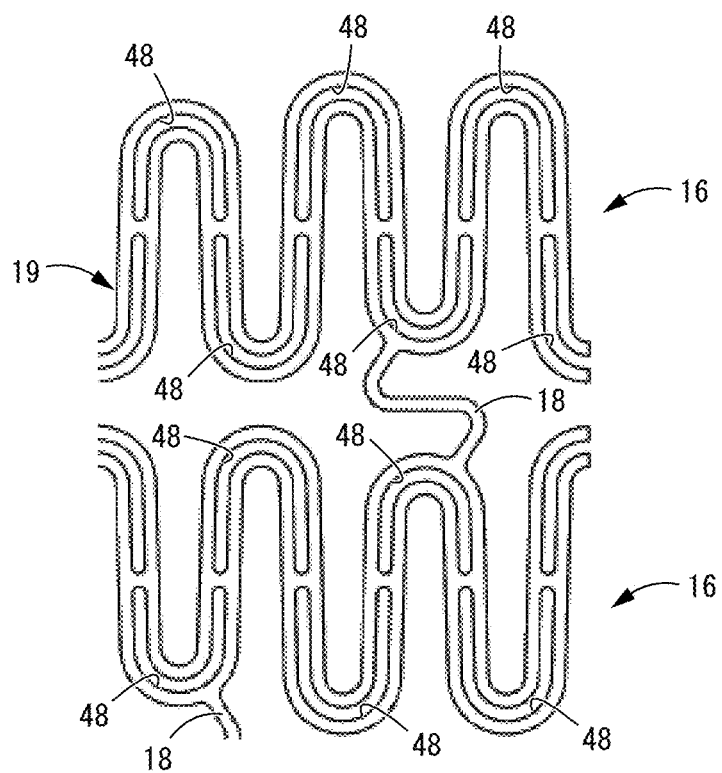
FIG. 23 is a front enlarged view showing a structural example of recesses employable in the stent of the present invention.

Also, as shown in FIG. 23, it is also possible to form a recess 48 on the stent skeleton, specifically, the strut 19 or the link part 18. In specific terms, when the stent is formed by electroforming, it is possible to implement processing of forming a projection or the like on the surface of the molding base, for example, and by so doing, it is possible to transfer a recess of a size corresponding to the inner circumference surface of the stent formed by electrodeposition onto that surface. Also, by forming an island-shaped mask on the center part of the surface of the skeleton formed by electroforming in advance and then implementing electroforming, a peripheral wall that encloses the island mask part is formed by electroforming, and it is possible to form a recess that opens at the outer circumference surface of the stent at that center mask part. This kind of recess 48 can be formed in any shape or size, and in addition to the groove shape extending in the lengthwise direction of the strut 19 or the link part 18 such as shown in FIG. 23, can also be a hole that is circular or the like. When this stent is produced by electroforming, by suitably setting the molding base or mask shape or the like used for electroforming, it is possible to form a recess of any size on the surface, and possible to greatly ensure the degree of freedom of design.

Furthermore, when forming the stent by electroforming, for example, it is possible to use eutectoid plating technology that uses an electrolytic solution in which a non-conductive powder is dispersed, and to give to the strut 19 or the link part 18 a porous structure or microporous structure corresponding to the eutectoid microparticles.

By forming the strut 19 or the link part 18 having the recess 48 or porous structure in this way, it is possible to reduce the metal volume for constituting the stent. Also, by carrying the drug in the recess 48 or the porous structure, it is possible to constitute a drug elution stent such as described above, for example, and to elute the drug effectively in the blood vessel wall.

Furthermore, the recess 48 formed on the stent can be not only a shape having a bottom, but also a through hole. By forming a through hole on the stent in this way, in addition to being able to more easily carry the drug, it is also possible to increase the volume of the drug carried. Also, after the drug or the like is eluted, the through hole becomes a cavity, making it possible to have blood pass through the inside of the through hole. Accordingly, the blood flow will not be obstructed compared to when the recess has a bottom, for example, and it is possible to even further exhibit the effect of the present invention of preventing turbulence or restenosis.

It is also possible to directly put a drug inside the recess 48, and for example, also possible to place a biodegradable resin cotton impregnated with the drug, or a capsule in which the drug is sealed inside the recess 48.

Yet further, whereas the dents and bumps formed on the stent can also be directly formed on the surface of the stent, for example by forming convex parts on the surface of the stent, it is also possible to form a part that is relatively concave.

Naturally, the stent does not have to be formed by electroforming, and for example, it is also possible to form the stent by implementing laser processing on a tube made of metal. In such a case, it is possible to directly obtain a strut with a cross section shape of a quadrangle ADEB by laser processing. Alternatively, it is also possible to implement laser processing on the metal tube so as to have a large central angle α for the outer circumference surface at first, obtain a strut with a cross section shape of a quadrangle AD'E'B, and then, implement laser processing on the side surfaces of that strut in order to have the central angle of the inner circumference surface be β size, or in other words, to have the included angle of both side surfaces be θ, thereby forming the strut for which the cross section shape is a quadrangle ADEB. Then, by implementing chamfering on the edge parts of the strut obtained in this way, it is possible to obtain the strut with the roughly reverse triangle cross section shape as shown in FIG. 4B described previously. In FIG. 9, arcs Co and Ci are respectively the metal tube outer circumference surface and inner circumference surface. Also, after forming these by electroforming so as to have a large central angle α of the outer circumference surface, for example, it is also possible to implement laser cutting so as to have a small central angle β of the inner circumference surface or so that the included angle of the inner circumference surfaces is θ. Namely, it would be acceptable to implement both of processes using electroforming and laser cutting when manufacturing the stent. Furthermore, it is not necessary to form the recess 48 that is formed on the stent by electroforming, and for example simultaneous with forming the stent, or after forming it, it is possible to form through holes as the recesses by laser processing or the like.

Furthermore, the stents 10, 20, 30, 32, 34, 36, and 42 noted in the embodiments above are all initial shapes, and when inserted in a lumen such as a blood vessel or the like, these are deformed with diameter reduction and delivered by catheter. When these stents 10, 20, 30, 32, 34, 36, and 42 are balloon expansion types, by being expanded using the balloon, they are placed in a state pressing against the inner circumference surface of the blood vessel. On the other hand, if they are self-expanding types using a metal material, they automatically expand when released from the delivery catheter. It is also possible to have the stent be roughly the initial shape in the expanded state, and in this case, the expansion state shape is manifested stably, and distortion and residual stress in the expanded and placed state are effectively suppressed. However, the present invention is not limited to that kind of mode, and it is also possible to form the stent having an initial shape of a different diameter dimension from the shape when placed.

Also, the stent shape is not limited to being a Y-shaped bifurcated shape, a tapered tube shape, an end-part thick shape, or a simple straight shape or the like as shown by way of example with the embodiments above, and the present invention can also be applied to various types of heteromorphic stents, such as a stent for which the diameter dimensions of the base tube part and the bifurcated tube part differ, a stent for which at least one of the base tube part and the bifurcated tube part is a tapered tube shape, a stent that is partially tapered in the lengthwise direction, a stent for which a thick part is provided at the lengthwise end part or the center part or the like.

Yet further, with the fifth embodiment, the rigidity was increased by both end parts in the axial direction being thick, but it is also possible to make the rigidity of both end parts in the axial direction greater by using a metal with high rigidity for both end parts in the axial direction for the straight shaped stent of the fourth embodiment, or by using a metal with high rigidity for both end parts in the axial direction with the thickness dimension being roughly constant over the entire axial length with the stent of the fifth embodiment.

Furthermore, with the skeleton of the stent, the strut 19 and the link part 18 may have different cross section shapes. Naturally, with the stent of the present invention, the link part is not absolutely essential, and it is also possible to continuously connect the annular parts adjacent in the axial direction of the stent through a helical structure. In this way, when not providing link parts, the stent skeleton is constituted only by the strut.

Yet further, the thickness dimension of the strut does not have to be uniform across the entire length. For example, in the lengthwise direction of the strut, it is also possible to make some portions thick or thin. Also, when not providing the link part as noted above, it is possible to form weak parts by means of the thin parts of the strut.

With the fourth to sixth embodiments, shown by example was roughly a reverse triangle as a shape for which the circumferential width dimension of the cross section shape of the strut 19 gradually becomes smaller from the outer circumference side toward the inner circumference side. However, the cross section shape thereof may be a reverse trapezoid, for example, or may be a semicircle shape which is convex to the inner circumference side. Naturally, with the present invention, as with the stent 42 of Example 2 described previously, it is also possible to have the heteromorphic structure for which the circumferential width dimension of the skeleton cross section gradually becomes larger from the outer circumference side toward the inner circumference side. For such a shape as well, in addition to the roughly triangular shape shown by example, it is also possible to use a trapezoid or a semicircle which is convex to the outer circumference side, for example. By so doing, by making the pressing surface area of the stent outer circumference surface on the blood vessel small and having the pressing force act in a concentrated location, the positioning effect of the stent on the blood vessel is increased, and it is possible to inhibit position skew of the stent when doing expansion or the like using a balloon or the like. Also, since the pressing force on the blood vessel wall acts in concentrated form, not only is it possible to exhibit the expansion effect effectively on the blood vessel that has hardened such as with calcified lesions, but it is also possible to expand to a desired dimension with a smaller expansion force on an unhardened blood vessel as well.

Furthermore, the present invention can also have a heteromorphic structure for which the circumferential width dimension of the skeleton cross section is made larger at the center part of the stent radial direction and gets gradually smaller toward both the outer circumference side and the inner circumference side, specifically, a rhombic-shaped cross section, a circular cross section, or an elliptical cross section would also be employable, for example. By so doing, while inhibiting mutual interference in the circumference direction at the inner circumference ends of the skeletons adjacent to each other in the circumference direction, which tends to be an obstacle during diameter reduction of the stent, it is possible to improve the positioning performance by having the pressing force on the blood vessel act in concentrated form at the outer circumference surface of the skeleton, and to improve the expansion performance of the blood vessel.

Also, with the present invention, the stent can be manufactured by etching technology rather than laser cutting or electroforming as described previously. Etching technology includes the technology described hereafter, for example. First, a molding base having the target stent shape and size is prepared. Next, on the surface of this molding base, a corrosion resistant mask is implemented in a shape corresponding to the plurality of annular parts and link parts, and at the part that is not masked, the molding base is exposed. Then, the molding base is immersed in a polishing liquid constituted by a strong acid, strong alkali, strong oxidant or the like, and by corroding and dissolving the part of the molding base that is not masked, a stent of the target structure as described above can be obtained.

With the etching technology, the stent is manufactured by corroding and dissolving the part of the molding base that is not masked. Thus, the thickness of the molding base is almost equal to the thickness of the finished product, and it is possible to make the thickness of the finished product large without spending a lot of time. Also, with the etching technology, since a liquid sample exclusively for electroforming is not needed, there is a higher level of selectability for the materials. Furthermore, with etching technology, since an electric current does not need to be flowed, electrical adjustment of the current density, voltage, or the like is not necessary, and setting and control of the manufacturing conditions are easy. With the present invention, it is also possible to form the skeleton by suitably combining laser cutting, electroforming, and etching. For example, it is also possible to implement the etching process partially on the skeleton formed by electroforming, or the like.

KEYS TO SYMBOLS 10, 20, 30, 32, 34, 36, 42: Stent, 13: Bifurcation, 16: Annular part, 18: Link part (weak part), 19: Strut, 48: Recess

The invention claimed is:

1. A stent comprising a structure of a skeleton that is expandable and contractible in a radial direction so as to have a tubular shape, the stent being configured to be placed in a body lumen, wherein
the skeleton has a heteromorphic structure due to changes of a cross section shape thereof in a thickness direction, the cross section shape of the skeleton has a triangle shape with three straight surfaces for which a width dimension becomes larger from an inner circumference surface thereof toward an outer circumference surface thereof, and
the skeleton is a metal skeleton comprising first and second annular parts that are formed integrally by electroforming using a different type of metal for each annular part and that have different rigidities.

2. The stent according to claim 1, wherein with the cross section shape of the skeleton, a corner of an inner circumference side has an arcuate curved surface.

3. The stent according to claim 1, wherein with the cross section shape of the skeleton, two of the straight surfaces are side surfaces and an included angle of both side surfaces in a circumference direction is greater than a central angle of an arc of an outer circumference surface thereof.

4. The stent according to claim 1, wherein
the stent has a heteromorphic tubular shape whose entire cross section shape changes in a lengthwise direction, and includes a metal skeleton formed by electroforming.

5. The stent according to claim 4, wherein a bifurcation is provided so that the stent has the heteromorphic tubular shape for which a number of tube parts changes in the lengthwise direction.

6. The stent according to claim 4, wherein the stent has the heteromorphic tubular shape for which a diameter dimension changes in the lengthwise direction.

7. The stent according to claim 1, wherein the first annular part is located at an end part of the skeleton in an axial direction and wherein the second annular part is located at a center part of the skeleton and has a rigidity that is less than a rigidity of the first annular part.

8. The stent according to claim 7, wherein the first annular part for which the rigidity is greater than that of the second annular part has a terminal part of lesser rigidity than the second annular part that is formed integrally with the first and second annular parts by electroforming.

9. The stent according to claim 1, wherein the skeleton has a laminated structure of a plurality of types of metals.

10. The stent according to claim 1, wherein a weak part for which strength is made lower is formed in the skeleton by at least one of electroforming and etching.

11. The stent according to claim 10, wherein the weak part has a smaller cross section area than that of other parts of the skeleton so as to be easily deformable.

12. The stent according to claim 1, wherein a recess is provided on a surface of the skeleton.

13. The stent according to claim 1, wherein the triangle shape has three corners.

14. The stent according to claim 13, wherein the corners are rounded.

15. The stent according to claim 1, wherein the triangle shape has an isosceles triangle shape.

16. The stent according to claim 1, wherein the central angle of the arc of the outer circumference side is in a range of 4° to 15°.

17. The stent according to claim 16, wherein the included angle is in a range of 30° to 100°.

18. The stent according to claim 1, wherein the triangle shape has an equilateral triangle shape.

19. The stent according to claim 7, wherein the first annular part is formed of a first metal having a first rigidity and the second annular part is formed of a second metal different than the first metal and having a second rigidity less than the first rigidity.

20. The stent according to claim 1, wherein the first and second annular parts are coupled via a strut having a thickness that is less than a thickness of at least one of the first and second annular parts.

21. A stent comprising a structure of a skeleton that is expandable and contractible in a radial direction so as to have a tubular shape, the stent being configured to be placed in a body lumen, wherein:
- the skeleton has a heteromorphic structure due to changes of a cross section shape thereof in a thickness direction,
- the cross section shape of the skeleton has a triangle shape with three straight surfaces for which a width dimension becomes larger from an inner circumference surface thereof toward an outer circumference surface thereof,
- the skeleton is a metal skeleton formed by electroforming, and
- the skeleton has a laminated structure of a plurality of types of metals such that a metal of a surface layer part of the laminated structure comprises at least one of Au and Pt and is different from a metal of a core part of the laminated structure.

* * * * *

UNITED STATES PATENT AND TRADEMARK OFFICE
CERTIFICATE OF CORRECTION

PATENT NO. : 10,137,014 B2
APPLICATION NO. : 15/103645
DATED : November 27, 2018
INVENTOR(S) : Yoshihiko Sano et al.

Page 1 of 1

It is certified that error appears in the above-identified patent and that said Letters Patent is hereby corrected as shown below:

In the Specification

Column 19, Line 18, delete "lit"

Signed and Sealed this
Twelfth Day of March, 2019

Andrei Iancu
*Director of the United States Patent and Trademark Office*